US012671576B2

(12) United States Patent
Soriente et al.

(10) Patent No.: US 12,671,576 B2
(45) Date of Patent: Jun. 30, 2026

(54) SECURE AGGREGATION WITH INTEGRITY VERIFICATION

(71) Applicant: NEC Laboratories Europe GmbH, Heidelberg (DE)

(72) Inventors: Claudio Soriente, Heidelberg (DE); Giorgia Marson, Heidelberg (DE)

(73) Assignee: NEC CORPORATION, Tokyo (JP)

( * ) Notice: Subject to any disclaimer, the term of this patent is extended or adjusted under 35 U.S.C. 154(b) by 221 days.

(21) Appl. No.: 18/481,263

(22) Filed: Oct. 5, 2023

(65) Prior Publication Data

US 2024/0396718 A1 Nov. 28, 2024

Related U.S. Application Data

(60) Provisional application No. 63/469,076, filed on May 26, 2023.

(51) Int. Cl.
*H04L 9/08* (2006.01)
*G16H 10/60* (2018.01)
*H04L 9/00* (2022.01)

(52) U.S. Cl.
CPC .............. *H04L 9/085* (2013.01); *H04L 9/008* (2013.01); *H04L 9/0869* (2013.01); *G16H 10/60* (2018.01)

(58) Field of Classification Search
None
See application file for complete search history.

(56) References Cited

U.S. PATENT DOCUMENTS

| | | | | |
|---|---|---|---|---|
| 2021/0336789 | A1* | 10/2021 | Chalkias | ............... H04L 9/3239 |
| 2022/0374544 | A1* | 11/2022 | Polychroniadou | ............................ G06F 21/6245 |
| 2022/0374762 | A1* | 11/2022 | Radhakrishnan | ...... G06N 20/00 |
| 2023/0109352 | A1* | 4/2023 | Wang | ...................... H04L 9/008 713/153 |

(Continued)

OTHER PUBLICATIONS

Yiping Ma and Jess Woods and Sebastian Angel and Antigoni Polychroniadou and Tal Rabin, Flamingo: Multi-Round Single-Server Secure Aggregation with Applications to Private Federated Learning, , https://eprint.iacr.org/2023/486, pp. 1-27 (Year: 2023).*

(Continued)

*Primary Examiner* — Rupal Dharia
*Assistant Examiner* — Shadi H Kobrosli
(74) *Attorney, Agent, or Firm* — Leydig, Voit & Mayer, Ltd.

(57) ABSTRACT

A method for secure aggregation, by a server, of client-provided inputs includes receiving, from each of a plurality of clients, a respective client input, for which a commitment is published. The commitments were computed using randomness and are aggregated by at least two super-clients and a sum of the aggregated commitments is published by each super-client. A sum of the received client inputs is published such that validity of the sum is checkable, by the clients, by comparing the sum of the received client inputs to a verification algorithm result that uses a sum of additive shares computed by the clients using the randomness, and by verifying that the published sum of the aggregated commitments is the same for each super-client. The method can be applied to use cases, for example, in digital medicine using medical data or smartcity applications to support decision-making.

20 Claims, 6 Drawing Sheets

(56)  References Cited

U.S. PATENT DOCUMENTS

| | | | | |
|---|---|---|---|---|
| 2023/0269090 | A1* | 8/2023 | Palakodety | H04L 9/3247 |
| | | | | 713/189 |
| 2024/0146690 | A1* | 5/2024 | Maia | H04L 63/083 |
| 2024/0289638 | A1* | 8/2024 | Avestimehr | G06N 3/098 |
| 2024/0291633 | A1* | 8/2024 | Zizzo | H04L 9/008 |
| 2025/0047296 | A1* | 2/2025 | Galvin | G06N 20/00 |
| 2025/0258951 | A1* | 8/2025 | Thompson | G06F 21/6218 |

OTHER PUBLICATIONS

Julien Mirval, Luc Bouganim, and Julian Sandu-Popa. 2021. Practical Fully-Decentralized Secure Aggregation for Personal Data Management Systems. In Proceedings of the 33rd International Conference on Scientific and Statistical Database Management (SSDBM '21). Association for Computing Machinery (Year: 2021).*

Timothy Stevens and Joseph Near and Christian Skalka, Secret Sharing Sharing For Highly Scalable Secure Aggregation, https://arxiv.org/pdf/2201.00864 (Year: 2022).*

Hannah Davis and Christopher Patton and Mike Rosulek and Phillipp Schoppmann, Verifiable Distributed Aggregation Functions, https://eprint.iacr.org/2023/130 (Year: 2023).*

Bell, James et al.; "Secure Single-Server Aggregation with (Poly)Logarithmic Overhead"; *CCS 2020: Proceedings of the 2020 ACM SIGSAC Conference on Computer and Communications Security*, Nov. 2, 2020; pp. 1253-1269; ACM Publications; New York, NY, USA.

Cortier, Véronique et al.; "Distributed ElGamal à la Pedersen—Application to Helios"; *Proceedings of the ACM Conference on Computer and Communications Security*, Nov. 4, 2013; pp. 131-142; ACM Publications; New York, NY, USA.

Ambrona, Miguel et al.; "Controlled Functional Encryption Revisited: Multi-Authority Extensions and Efficient Schemes for Quadratic Functions"; *Proceedings on Privacy Enhancing Technologies;* Jan. 2021; pp. 21-42; vol. 1; Sciendo; Warsaw, Poland.

* cited by examiner

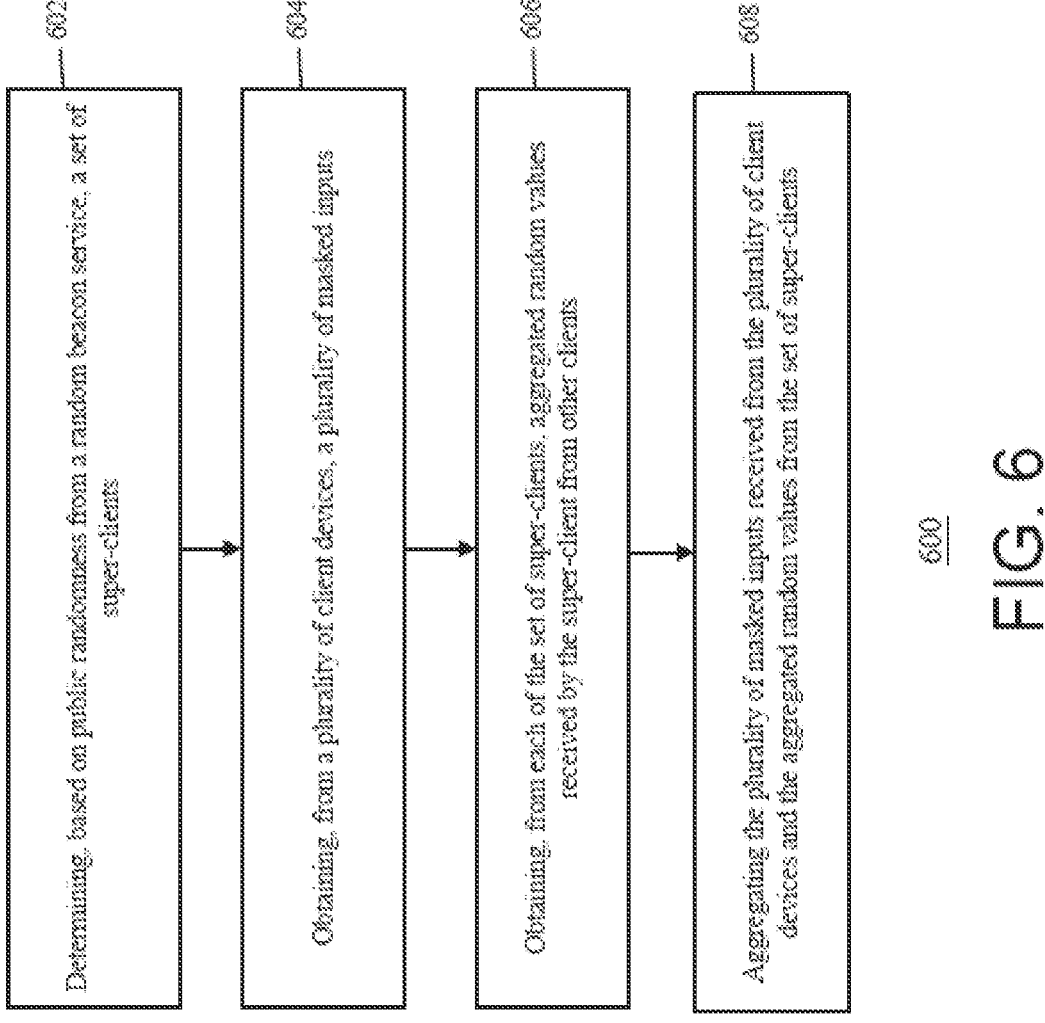

602 — Determining, based on public randomness from a random beacon service, a set of super-clients 604 — Obtaining, from a plurality of client devices, a plurality of masked inputs 606 — Obtaining, from each of the set of super-clients, aggregated random values received by the super-client from other clients 608 — Aggregating the plurality of masked inputs received from the plurality of client devices and the aggregated random values from the set of super-clients

SECURE AGGREGATION WITH INTEGRITY VERIFICATION

CROSS-REFERENCE TO RELATED APPLICATION

Priority is claimed to U.S. Provisional Patent Application No. 63/469,076, filed on May 26, 2023 the entire disclosure of which is hereby incorporated by reference herein.

FIELD

The present invention relates to a method, system and computer-readable medium for secure aggregation.

BACKGROUND

Secure aggregation can allow a server to compute the sum of client-provided inputs, without revealing individual client inputs to any party. Secure aggregation protocols are widely used for privacy-preserving federated learning applications.

Secure aggregation can allow a set of clients to compute the sum of their inputs while keeping each party's input private. In single-server secure aggregation protocols, clients may not have direct communication channels with each other, and the aggregation protocol may be orchestrated by a server the communicates with each client and forwards relevant messages. Single-server secure aggregation was introduced as a privacy-friendly mechanism for federated learning applications to prevent the server from learning individual inputs provided by clients. In particular, many secure aggregation solutions target strong privacy guarantees but offer little or no integrity protection against a possibly malicious server that tampers with the sum of clients' inputs.

SUMMARY

In an embodiment, the present disclosure provides a computer-implemented method for secure aggregation, by a server of a distributed client-server application, of client-provided inputs in a manner allowing for integrity verification. The method includes receiving, from each of a plurality of clients, a respective client input, for which a commitment to the respective client input is published. The commitments have been computed using randomness, and the commitments are aggregated by at least two super-clients and a sum of the aggregated commitments is published by each of the at least two super-clients. The method also includes obtaining a sum of the received client inputs. The method also includes publishing the sum of the received client inputs such that a validity of the sum of the received client inputs is checkable, by one or more of the clients, by comparing the sum of the received client inputs to a result of a verification algorithm that uses a sum of additive shares that were computed by the clients using the randomness, and by verifying that the published sum of the aggregated commitments is the same for each of the at least two super-clients. The method can be applied to use cases, for example, in digital medicine using medical data or smartcity applications to support decision-making.

BRIEF DESCRIPTION OF THE DRAWINGS

Embodiments of the present invention will be described in even greater detail below based on the exemplary figures. The present invention is not limited to the exemplary embodiments. All features described and/or illustrated herein can be used alone or combined in different combinations in embodiments of the present invention. The features and advantages of various embodiments of the present invention will become apparent by reading the following detailed description with reference to the attached drawings which illustrate the following:

FIG. 6 illustrates a process for secure aggregation with public randomness according to an embodiment of the present disclosure.

DETAILED DESCRIPTION

Figure 1:
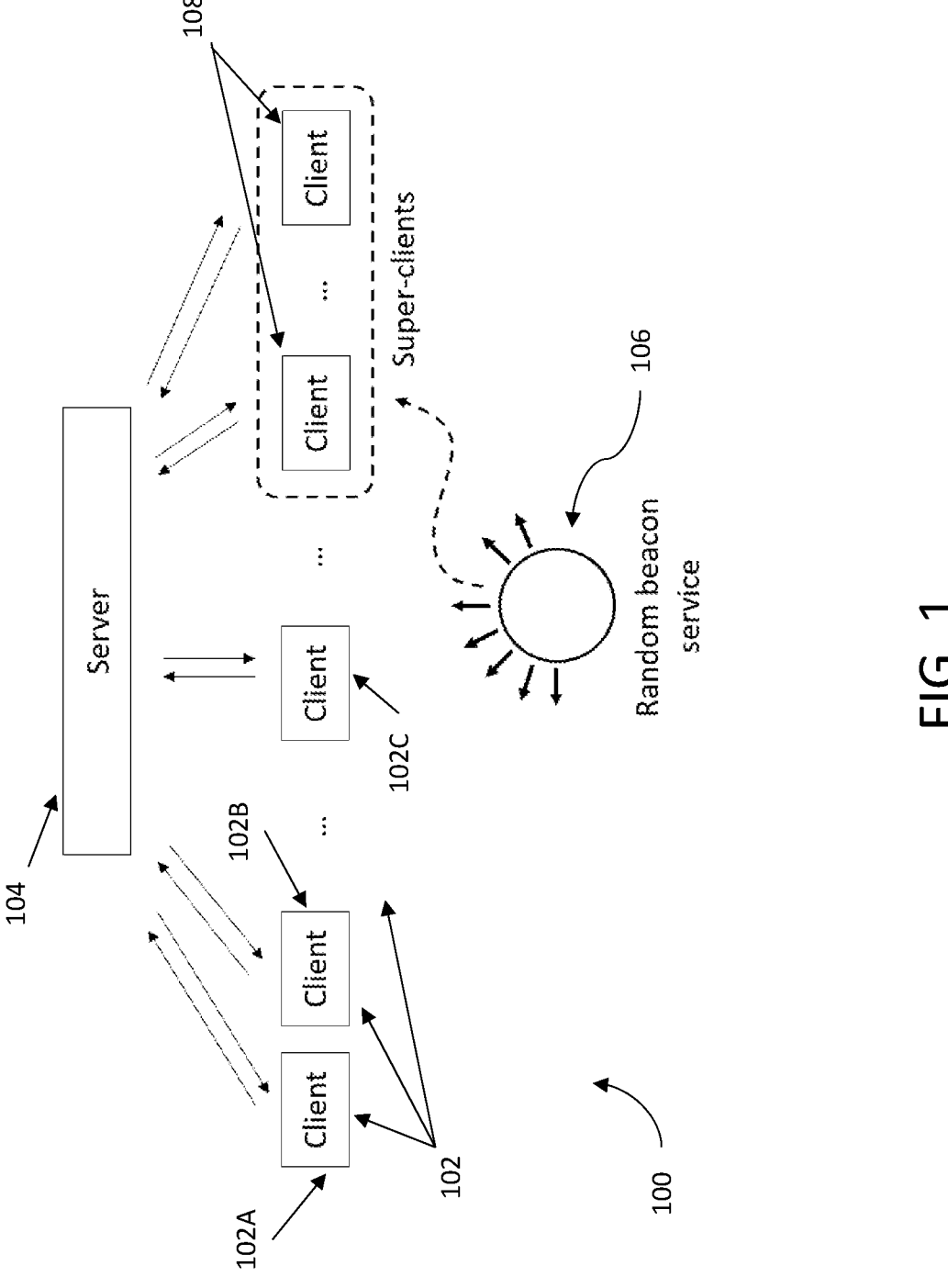
FIG. 1 schematically illustrates an exemplary environment of entities involved in a secure aggregation protocol.

Embodiments of the present invention provide improvements to an efficient secure aggregation protocol and framework that leverages a random beacon service to select a subset of clients that aid the server to aggregate inputs. Embodiments of the present invention provide for improvements to secure aggregation protocols and frameworks by providing input integrity, e.g., assurance that the sum output by the protocol was computed correctly.

Embodiments of the present invention can use linearly-homomorphic commitments to improve the secure aggregation protocol and framework with the ability for clients to verify whether the sum of client-provided inputs, as published by the server, has been computed correctly. Embodiments of the present invention also provide a method for enhancing secure aggregation protocols (e.g., single server protocols) with integrity protection. Embodiments of the present invention can further enable each client who participates in the aggregation process to verify that the output of the SA protocol, as declared by the server, matches with the sum of the client provided inputs.

In an example secure aggregation protocol, each client provides a private input so that the server can learn the sum of all client-provided inputs without learning individual inputs. The sum as computed by the server is then shared with the clients. Embodiments of the present invention can enable clients to verify that the sum published by the server is the actual sum of the inputs provided by the clients.

In a first aspect, the present disclosure provides a computer-implemented method for secure aggregation, by a server of a distributed client-server application, of client-provided inputs in a manner allowing for integrity verification. The method includes receiving, from each of a plurality of clients, a respective client input, for which a commitment to the respective client input is published. The commitments have been computed using randomness, and the commitments are aggregated by at least two super-clients and a sum of the aggregated commitments is published by each of the at least two super-clients. The method also includes obtaining a sum of the received client inputs. The method also includes publishing the sum of the received client inputs such that a validity of the sum of the received client inputs is checkable, by one or more of the clients, by comparing the sum of the received client inputs to a result of a verification algorithm that uses a sum of additive shares that were computed by the clients using the randomness, and by verifying that the published sum of the aggregated commitments is the same for each of the at least two super-clients.

In a second aspect, the present disclosure provides the method according to the first aspect, wherein the at least two super-clients, and/or at least two other super-clients, receive and publish different additive shares of a same client along with additional additive shares from other clients such that no super-client obtains all additive shares of a same client, and such that the sum of all additive shares is obtainable by summing the additive shares published by the at least two super-clients and/or the at least two other super-clients.

In a third aspect, the present disclosure provides the method according to the first or second aspect, wherein a number of the super-clients to be used for the secure aggregation is determined from a random beacon, and wherein a number of the additive shares computed per client corresponds to the number of the super-clients such that each of the super-clients receives one additive share per client.

In a fourth aspect, the present disclosure provides the method according to any of the first to third aspects, wherein the number of the super-clients to be used for the secure aggregation is determined using a pseudo-random function which takes as input a random seed generated by the random beacon and public keys of the clients.

In a fifth aspect, the present disclosure provides the method according to any of the first to fourth aspects, wherein the randomness is different for different clients, and wherein the randomness can only be reconstructed if all of the additive shares for a respective one of the clients are available.

In a sixth aspect, the present disclosure provides the method according to any of the first to fifth aspects, wherein at least one backup client is selected for each of the at least two super-clients. The backup client in each case has a secret key of a corresponding one of the super-clients.

In a seventh aspect, the present disclosure provides the method according to any of the first to sixth aspects, wherein the server receives the secret key from the corresponding one of the super-clients and sends the secret key to a corresponding one of the backup clients.

In an eighth aspect, the present disclosure provides the method according to any of the first to seventh aspects, wherein a set of backup clients are selected for each of the at least two super-clients, and wherein a secret sharing reconstruction threshold is less than a number of backup clients in the set so as to allow for a dropout of at least one of the at least two super-clients.

In a ninth aspect, the present disclosure provides the method according to any of the first to eighth aspects, wherein the client inputs are blinded using a mask using a key shared with one of the at least two super-clients.

In a tenth aspect, the present disclosure provides the method according to any of the first to ninth aspects, further comprising receiving, from each of the at least two super-clients, a partial blinding that was computed by a respective one of the super-clients by summing the masks received by the respective super-client from different ones of the clients. Obtaining the sum of the received client inputs includes aggregating the blinded client inputs and subtracting a sum of the partial blindings.

In an eleventh aspect, the present disclosure provides the method according to any of the first to tenth aspects, wherein the commitments are determined using a linearly-homomorphic commitment scheme.

In a twelfth aspect, the present disclosure provides the method according to any of the first to eleventh aspects, wherein the client inputs are from medical records and/or independent healthcare facilities, and wherein the sum of the received client inputs is used for training a model for medical diagnostics or for monitoring health status of patients.

In a thirteenth aspect, the present disclosure provides the method according to any of the first to twelfth aspects, wherein the client inputs are from sensors of a smartcity application, and wherein the sum of the client inputs are used to determine a condition in the smartcity application.

In a fourteenth aspect, the present disclosure provides a computer system for secure aggregation, by a server of a distributed client-server application, of client-provided inputs in a manner allowing for integrity verification, the system comprising one or more hardware processors which, alone or in combination, are configured to provide for execution of the method according to any of the first to thirteenth aspects.

In a fifteenth aspect, the present disclosure provides a tangible, non-transitory computer-readable medium having instructions thereon for secure aggregation, by a server of a distributed client-server application, of client-provided inputs in a manner allowing for integrity verification, the instructions, upon being executed by one or more hardware processors, alone or in combination, providing for execution of the method according to any of the first to thirteenth aspects.

Embodiments of the present invention can use a set of k super-clients. Those are regular clients chosen randomly from the set of n clients. Their task is to help in the verification of the sum as published by the server. Super-clients can be chosen, for example, using a random beacon service 106, as depicted in the environment 100 of FIG. 1. For instance, a set of n clients 102 can communicate with a server 104. The random beacon service 106 can be used to obtain a random permutation of the client IDs, and the first k clients are selected as super-clients 18.

Referring to FIG. 1, the system 100 shows the entities involved in the secure aggregation protocols with public randomness. Embodiments of the present invention can use a random beacon service 106 to generate uniform randomness for selecting the super-clients 108 from the clients 102. In some instances, the backup clients of super-clients 108 can be generated using the uniform randomness from the random beacon service 106 as well. For example, according to some embodiments, a server 104 determines a set of super-clients 108 from the clients 102 based on evaluating a pseudo-random function (PRF) on input a random seed, generated by the random beacon service 106, and the public keys of all the clients 102. Similarly, each super-client 108 can be assigned a pseudo-randomly chosen set of backup clients. For instance, client 102A can also be a super-client 108 with one or more backup clients (e.g., other clients such as client 102B and/or 102C).

Super-clients 108 and backup clients aid the server 104 in computing the aggregation of client inputs throughout the protocol execution, while the rest of the clients 102 that are not also super-clients 108 only have to be active once to provide their inputs to the server 104. At a high level, each client 102 can provide a masked input to the server 104 and each super-client 108 can provide a partial output to the server 104. The server 104 can use these partial outputs to remove the masks of the masked inputs and recover the sum of client inputs. This method can guarantee that the inputs of each client remain private, in the sense that neither the server

104 nor any other client 102 can learn individual inputs (c.g., which input belongs to which of the clients 102). Moreover, should some of the super-clients drop out before being able to send their partial outputs to the server 104, their backup clients allow the server 104 to reconstruct the missing partial outputs and complete the protocol.

Although certain entities within system 100 are described herein in the FIGs. as being singular entities, it will be appreciated that the entities and functionalities discussed herein can be implemented by and/or include one or more entities (e.g., one or more servers). The entities within the system 100 are in communication with other devices and/or systems within the system 100 via a network. The network can be a global area network (GAN) such as the Internet, a wide area network (WAN), a local area network (LAN), or any other type of network or combination of networks. The network can provide a wireline, wireless, or a combination of wireline and wireless communication between the entities within the system 100.

The clients 102 can each include computing devices or sensors that are operated by a client, customer, and/or other individual that is associated with the server 104. Each user from system 100 is and/or includes, but is not limited to, a desktop, laptop, tablet, mobile device (e.g., smartphone device, or other mobile device), computing system, sensor, IoT device and/or other types of computing entities that generally comprises one or more communication components, one or more processing components, and one or more memory components.

The server 104 is a computing system that performs one or more functions described herein. For instance, the server 104 can include, execute, operate, and/or otherwise be configured to perform secure aggregation using public randomness. For instance, in operation, the server 104 obtains information (e.g., randomness such as a seed) from the random beacon service 106 and/or information from the users 102 (e.g., public keys). The server 104 determines super-clients and/or backup clients from the users 102 based on the information from the random beacon service 106 and/or the information from the users 102. Subsequently, based on determining the super-clients 108 and/or backup clients, the server 104 can perform secure aggregation. For instance, the super-clients 108 and/or the back-up neighbors can assist the server 104 in computing the aggregation of the inputs from the users 102 as well as additional users within the system 100. For example, the super-clients 108 are a subset of the clients 102 from system 100 that aid the server 104 in computing the aggregation of the inputs provided by the users of the system 100. Each super-client can include one or more back-up neighbors, and the back-up neighbors allow the server 104 to reconstruct missing partial outputs and complete the aggregation protocol if some super-clients drop out before being able to send their partial outputs to the server 104. This will be explained in further detail below.

The server 104 includes and/or is implemented using one or more computing devices, computing platforms, cloud computing platforms, systems, servers, and/or other apparatuses. In some instances, the server 104 can be implemented as engines, software functions, and/or applications. For example, the functionalities of the server 104 can be implemented as software instructions stored in storage (e.g., memory) and executed by one or more processors.

The random beacon service 106 can be a computing system that performs one or more functions described herein. For instance, the random beacon service 106 can provide trusted public randomness (e.g., a random seed for a PRF) to the server 104 and/or the users within the system

100. The random beacon service 106 includes and/or is implemented using one or more computing devices, computing platforms, cloud computing platforms, systems, servers, and/or other apparatuses. The random beacon service 106 may be a third party entity (e.g., an entity that is not associated with the server 104 and/or the users of the system 100). In some instances, the random beacon service 106 can be implemented as engines, software functions, and/or applications. For example, the functionalities of the random beacon service 106 can be implemented as software instructions stored in storage (e.g., memory) and executed by one or more processors.

Figure 2:
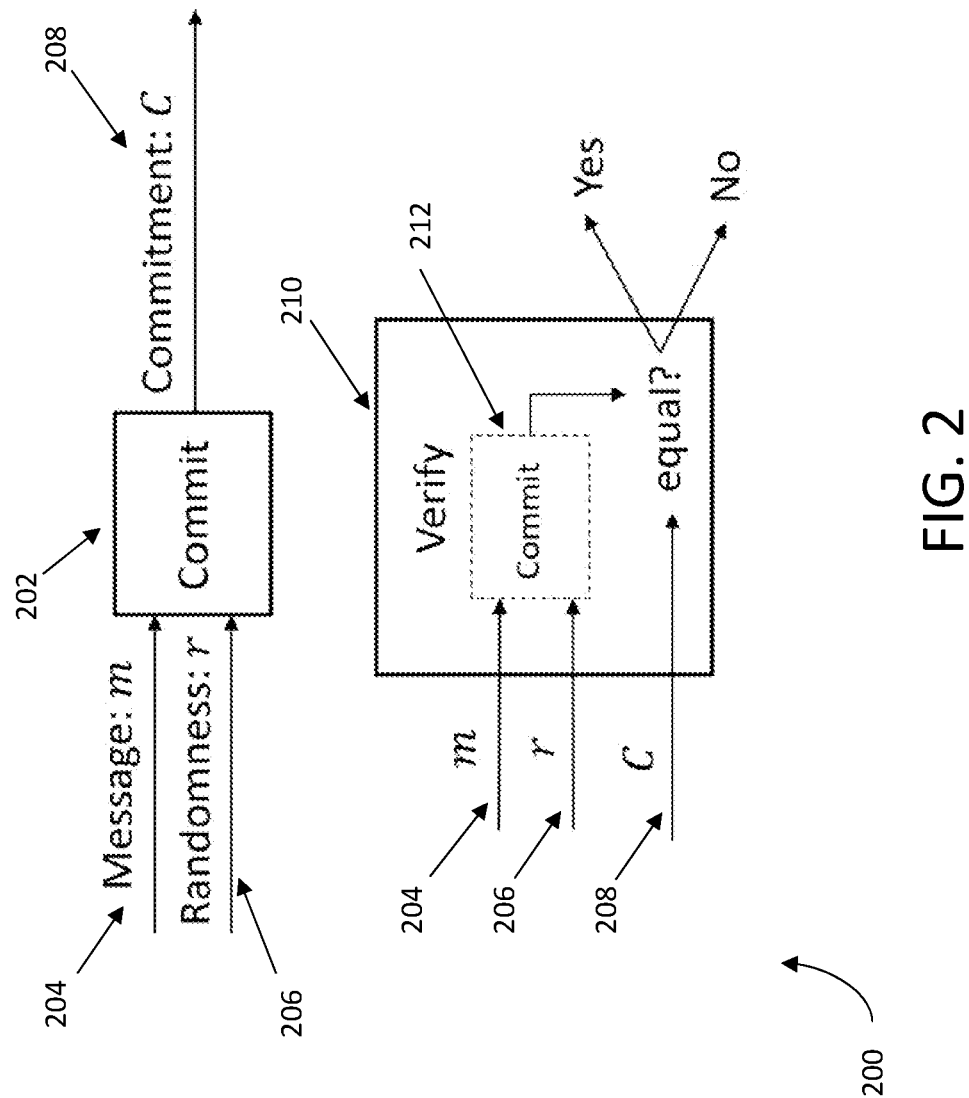
FIG. 2 illustrates an example of a functionality of a commitment scheme.

Embodiments of the current invention use linearly-homomorphic commitments. A commitment scheme COMM, as shown in FIG. 2, allows a party (e.g., a sender) to commit to a message m. Formally, a commitment scheme COMM comprises two algorithms, COMM.Commit and COMM.Verify. In order to commit to a message m, the sender can run algorithm COMM.Commit on input m and a uniformly chosen random value r (chosen by the sender), obtaining a commitment C, denoted by C:=COMM. Commit(m;r). Later on, the sender can open the commitment by revealing the input message m and the randomness r. Given values C, m, and r, any party can check that C is a valid commitment for message m by running algorithm COMM.Verify(C,m,r). A so-derived commitment C is hiding, e.g., it does not reveal any information about the message m, and it is binding, e.g., it is not possible to open commitment C to a message different from m. The specific format of the input values (i.e., message m, randomness r) and output values (. i.e., commitment C), and how the values are generated and/or chosen, can vary depending on the specific instantiation of the commitment scheme. In the example functionality 200 of FIG. 3, a commitment scheme 202 (i.e., function, algorithm) can receive, as inputs, a message m 204 and a randomness r 206. The commitment scheme 202 can process the message m 204 and randomness r 206 to output (i.e., determine) a commitment C 208. A verification scheme 210 (i.e., function, algorithm) can then receive, as inputs, the message m 204, the randomness r 206, and the commitment C 208. The verification scheme 210 can then verify that the commitment C 208 was properly computed using the message m 204, the randomness r 206. Additionally, most commitment schemes providing for the properties of linear homomorphism can be used to perform the COMM functionalities in different instantiations. For example, based on a given instantiation, different COMM.vrfy functions may verify as "yes," "1", "TRUE," or the equivalent.

In an example embodiment of a commitment scheme (e.g., a commitment scheme recalled due to Pedersen), p, $q \in \mathbb{N}$ where q is a large prime and p=2q+1 is a safe prime, $\mathbb{G}$ denotes a group of order q, and g, h are two generators of $\mathbb{G}$. To commit to a message $m \in \mathbb{Z}_q$, the sender can choose a value $r \in \mathbb{Z}_q$ uniformly at random and computes $C:=g^m \cdot h^r$. Given a commitment C, a message m and a random value r, a party can check if C is a valid commitment with respect to message m by evaluating the predicate $C \stackrel{?}{=} g^m \cdot h^r$. Then, COMM.Vrfy(C,y,r)=TRUE if and only if $C=g^y \cdot h^r$, where r is the randomness chosen by the sender. Afterwards, when providing the specification of the verifiable aggregation protocol, the verification algorithm COMM.Vrfy can take as randomness $\sum_{j \in \mathcal{K}} \rho_j$. Therefore, in the protocol for verifiable secure aggregation, multiple commitments can be combined, and the clients can verify the combined commitment using as randomness the sum of random values $\rho_j$ provided by super-clients.

A commitment scheme is linearly homomorphic if, when given commitment $C_1$ to message $m_1$ and commitment $C_2$ to message $m_2$, then it is possible to aggregate $C_1$ and $C_2$ in a commitment C that can be opened to message $m_1+m_2$. This is shown in FIG. 3.

In the following embodiments of the present invention, commi $=$COMM.Commit$(x_i;r_i)$ is used to denote the computation, performed by user i, of a commitment comm; for input message $x_i$ and randomness $r_i$.

Figure 3:
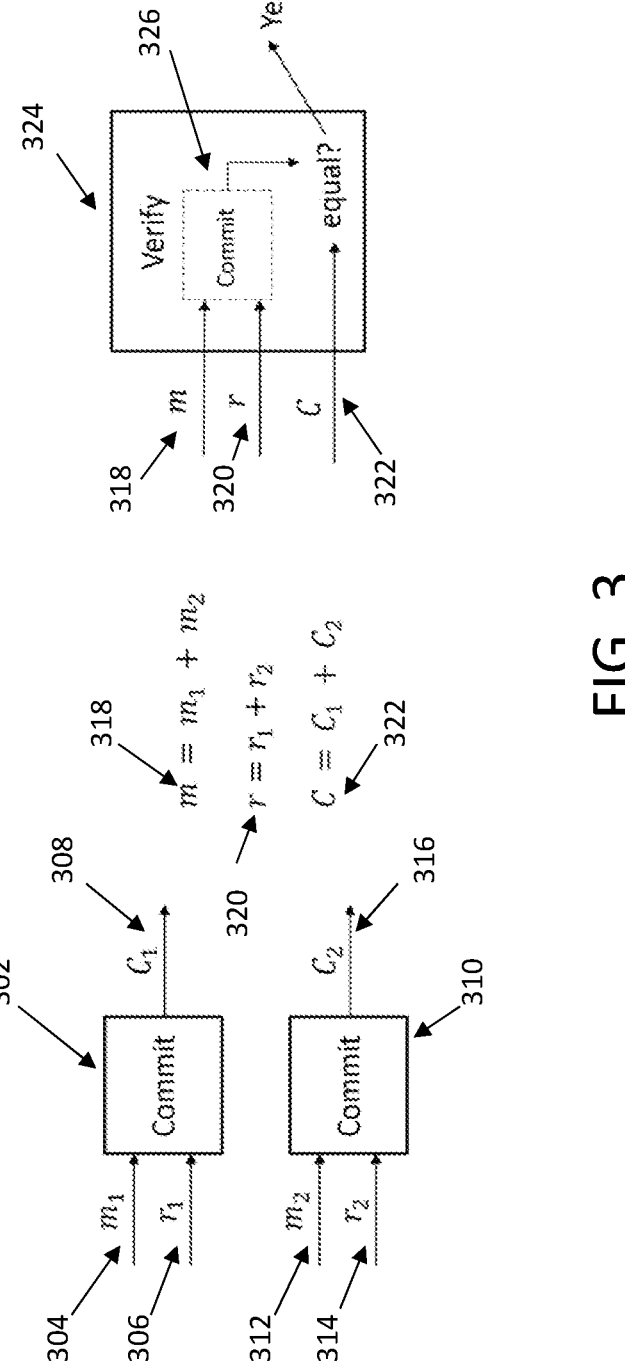
FIG. 3 illustrates an example of a functionality of a homomorphic commitment scheme.

In the example functionality 300 of FIG. 3, multiple commitment schemes can be employed, e.g., a different commitment C can be output for each individual message m and randomness r. For instance, a commitment scheme 302 can receive a message $m_1$ 304 and a randomness $r_1$ 306, which can be provided by a first client (e.g., a client i or a super-client j). The commitment scheme 302 can then output a commitment $_{C1}$ 308 by applying the randomness $r_1$ 306 to the message $m_1$ 304. A commitment scheme 310 (which is preferably the same commitment scheme as commitment scheme 302) can receive a message $m_2$ 312 and a randomness $r_2$ 314 provided by a second client. The commitment scheme 310 can then output a commitment $C_2$ 316. The messages 304, 312 can be summed into a message m 318, the randomnesses 306, 314 can be summed into a randomness r 320, and the commitments 308. 316 can be summed into a commitment C 322. A verification scheme 324 (e.g., function, algorithm) can then receive, as inputs, the message m 318, the randomness r 320, and the commitment C 322. The verification scheme 324 can run a further commitment scheme 326 (which is preferably the same commitment scheme as commitment schemes 302, 310), and verify whether the output of the further commitment scheme 326 is or is not equal to the commitment C 322.

In embodiments of the present invention, before clients share their inputs with the server, client i can compute the commitment to its input $x_i$ as comm$_i$:=COMM.Commit $(x_i,r_i)$. At the same time, client i can compute k random shares of randomness $r_i$ so that $r_i$ can be reconstructed only if all of the k shares are available. This could be done, for example, by selecting k−1 shares at random $r_{i2}$, . . . , $r_{ij}$, . . . ,$r_{ik}$ and then computing $r_i=r_i-(r_{i2}, . . . ,r_{ij}, . . . ,r_{ik})$. Next client i can send comm$_i$ to all the super-clients while it sends $r_{ij}$ to super-client j.

Super-client j can aggregate all received commitments comm$_1$, . . . , comm$_n$ as $C_j$ and publish the result (e.g., send $C_j$ to all clients when the server is sending the message and/or send to the server or requesting to forward to all clients when any entity other than the server is sending the message). At the same time, super-client j can aggregate all random shares received $r_{ij}$, . . . ,$n_j$ as $z_j$ and publish the result. Thus, as used herein, publishing means sending or making available to all clients (or super-clients depending on the situation), possibly using the server as an intermediary. As mentioned above, all communications between clients will typically go through the server as there is typically no communication channel between clients.

After the server publishes the sum y of client-provided inputs, each client can do the following. Each client can accept the sum y published by the server as valid when (a) all super-clients j have published the same value $C_j$, and COMM.Verify$(C_j;y;z)$ outputs "yes" (or 1 or TRUE, or the equivalent), where $z=z_1+z_2+ . . . +z_k$.

Figure 4:
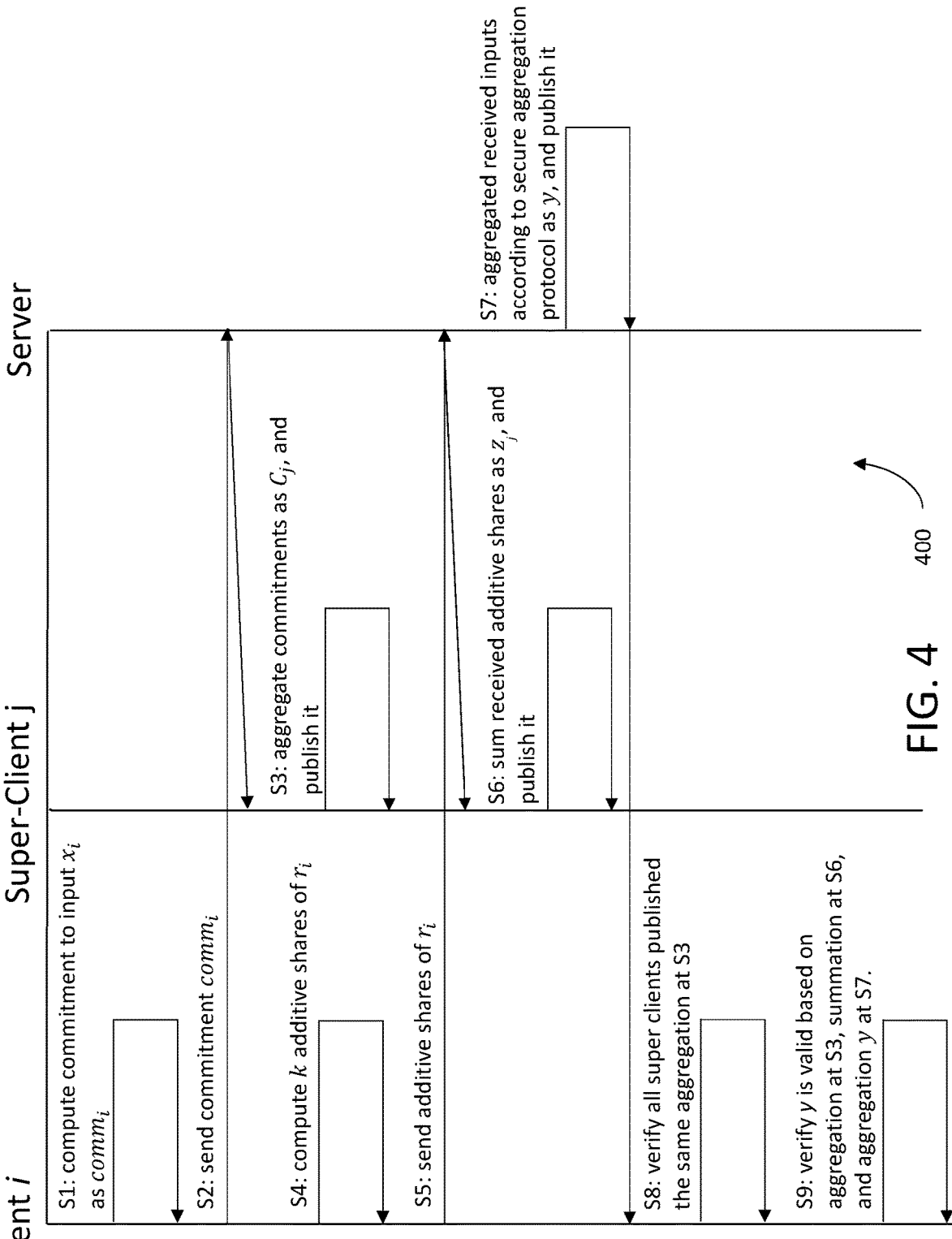
FIG. 4 illustrates an example process of a secure aggregation protocol with integrity.

In an embodiment, the present invention can provide for computing, by a server of a distributed client-server application, the sum of client-provided inputs while ensuring to clients that the computed sum as published by the server is the actual sum of the client-provided inputs. For example, a process for verifying a server output by a client can be seen in FIG. 4. While the steps of process 400, provided below, are numbered steps, the steps are not necessarily performed in that number order, and are capable of being performed in different order unless one step is required to be performed to provide information for a subsequent step. For example, step S7 can be performed before step S1, and the server can perform step S8 upon receiving the client inputs, or at a later time. Moreover, steps can be performed simultaneously, such as step S1 and S4.

At step S1, a client i with input $x_i$ can compute and publish a commitment to its input comm$_i$:=COMM.Commit$(x_i;r_i)$, where $r_i$ is the randomness used to obtain the commitment.

At step S2, a client sends a commitment comm; to the super-clients (e.g., via the server), a super-client can receive the commitment to input $x_i$. Since in most cases, the clients do not communicate with each other, the commitments are sent to the server, who sends them to the chosen super-clients.

At step S3, super-client j can aggregate all client commitments as $C_j$:=comm$_1$*comm$_2$* . . . *comm$_n$, where * denotes the commitment-aggregation operation, and publish the result of the aggregation.

At step S4, client i can computes k additive shares $r_{\{1,1\}}, . . . , r_{\{ik\}}$ of the randomness $r_i$.

At step S5, the client i can send each computed additive share to one of k super-clients j. Since in most cases, the clients do not communicate with each other, the commitments are sent to the server, who sends them to the chosen super-clients. Each client sends one additive share in each case to one of the k super-clients such that each super-client only receives one additive share per client.

At step S6, super-client j can sum all additive shares it receives as $z_j=r_{\{1,j\}}+r_{\{2,j\}}+ . . . +r_{\{n,ji\}}$ and publish the result.

At step S7, client i can send its blinded input $c_i$ to the sever, protected according to the secure aggregation protocol.

At step S7, the server can follow steps of the secure aggregation protocol to obtain the sum of all client inputs $y:=x_1+x_2+ . . . +x_n$ and publish the result.

At step S8, client i can verify that super-client j has published the same value $C_j$ in step S3 as all other super-clients.

At step S9, client i can verify that y is valid based on the aggregation at step S3, summation at step S6, and aggregation at step S7 (e.g., COMM.Vrfy$(C_j;y;z)$==1 where $z=z_1+z_2+ . . . +z_k$). Client i can accept the sum y published by the server as valid if the verifications of step S8 and S9 are true (e.g., the verification algorithms return TRUE). In other words, each of k super-clients can perform a partial sum of all of the additive shares and publish this partial sum. The verification algorithm can then sum up these published, partial sums. Upon receiving k partial sums $z_1, . . . , z_k$, client i can compute the overall sum $z=\Sigma_j z_j$ and then use the so-derived z as randomness in the COMM.Verify algorithm. With other words, the verification procedure at step S9 of FIG. 4 can comprise an aggregation step to derive z and a commitment verification step to verify that $C_j$ is a valid commitment for message y with randomness z.

Single-server secure aggregation protocols can be introduced as a privacy-enhancing mechanism for federated learning, a recent paradigm to enable the training of a machine-learning models using data obtained from distributed data sources without the need of collecting data in a centralized location. The federated learning paradigm has enabled many practically-relevant applications of artificial intelligence (AI).

In an embodiment of the present invention, federated learning can be used in the training of a global model for medical diagnostics based on a patients data provided by independent healthcare facilities. Relying on data from many different sources can allow for derivations of a more accurate model, however, keeping the individual models private is advantageous for protecting the privacy of patients.

In another embodiment of the present invention, federated learning can be used in healthcare leveraging of wearable devices (e.g., such as a smart-watches) to train a machine learning (ML) model for monitoring the health status of patients. Again, the prediction capabilities of the resulting ML model may rely on large amounts of sensitive data from different patients, which can raise privacy concerns.

In another embodiment of the present invention, privacy-preserving federated learning can also support business-oriented use cases. For instance, different financial institutions may benefit from training prediction models based on the data of all of their customers, without disclosing individual data.

Finally, secure aggregation protocols find applicability beyond federated learning. For instance, smart-city sensor data may be combined to compute information such as average temperature in a certain area, traffic information, etc.

In an embodiment, the present invention provides a method for computing, by a server of a distributed client-server application, the sum of client-provided inputs while ensuring to clients that the computed sum as published by the server is the actual sum of the client-provided inputs, the method comprising the steps of:

1) Client i with input $x_i$ computes and publishes commitment to its input $comm_i := COMM.Commit(x_i; r_i)$, where $r_i$ is the randomness used to obtain the commitment; client i also sends its input $x_i$ input to the sever, protected according to the secure aggregation protocol.

2) Client i computes k additive shares $r_{\{1,1\}}, \ldots, r_{\{i,k\}}$ of $r_i$ and sends each of them to one of k super-clients.

3) Super-client j aggregates all client commitments as $C_j := comm_1 * comm_2 * \ldots * comm_n$ and publishes the result.

4) Super-client j sums all additive shares it receives as $z_j = r_{\{1,j\}} + r_{\{2,j\}} + \ldots + r_{\{n,j\}}$ and publishes the result.

5) The server follows the step of the secure aggregation protocol to obtain the sum of all client inputs $y := x_1 + x_2 + \ldots + x_n$ and publishes the result.

6) Clients accept the sum y published by the server as valid if (a) all super-clients have published the same value in step 3, and (b) $COMM.Vrfy(C_j; y; z) == 1$ where $z = z_1 + z_2 + \ldots + z_k$.

Embodiments of the present invention can provide for the following improvements over existing technology:

1) Publishing, by a client of a distributed client-server application, a commitment to its input and sharing, by the same client, additive shares of the randomness used to compute the commitment to a set of super-clients.

2) Publishing by each of the super-clients the sum of all client commitments $C_j$ and the sum of all shares received by a client $z_j$.

3) Checking, by a client, that all super-clients have published the same $C_j$ and that a value y provided by the server with randomness $z = z_1 + z_2 + \ldots + z_k$ is a valid opening for commitment $C_j$.

4) In contrast to existing technology of integrity mechanisms for secure aggregation, which have communication complexity that is quadratic in the number of clients, embodiments of the present invention can advantageously provide that a client has to send or receive only $O(k)$ messages, with $k \ll n$.

Figure 5:
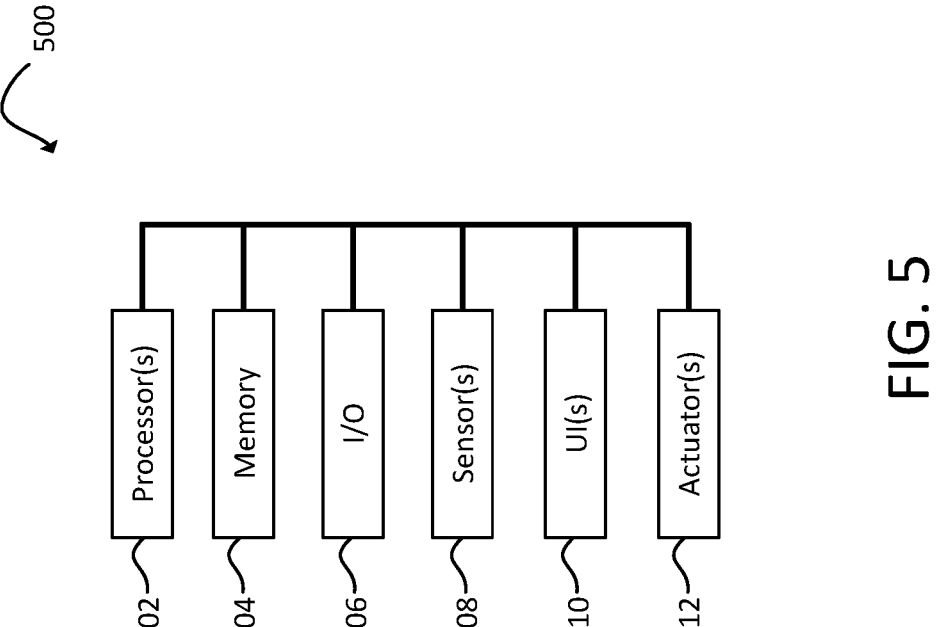
FIG. 5 is a block diagram of an exemplary processing system, which can be configured to perform any and all operations disclosed herein.

Referring to FIG. 5, a processing system 500 can include one or more processors 502, memory 504, one or more input/output devices 506, one or more sensors 508, one or more user interfaces 510, and one or more actuators 512. Processing system 500 can be representative of each computing system disclosed herein.

Processors 502 can include one or more distinct processors, each having one or more cores. Each of the distinct processors can have the same or different structure. Processors 502 can include one or more central processing units (CPUs), one or more graphics processing units (GPUs), circuitry (e.g., application specific integrated circuits (ASICs)), digital signal processors (DSPs), and the like. Processors 502 can be mounted to a common substrate or to multiple different substrates.

Processors 502 are configured to perform a certain function, method, or operation (e.g., are configured to provide for performance of a function, method, or operation) at least when one of the one or more of the distinct processors is capable of performing operations embodying the function, method, or operation. Processors 502 can perform operations embodying the function, method, or operation by, for example, executing code (e.g., interpreting scripts) stored on memory 504 and/or trafficking data through one or more ASICs. Processors 502, and thus processing system 500, can be configured to perform, automatically, any and all functions, methods, and operations disclosed herein. Therefore, processing system 500 can be configured to implement any of (e.g., all of) the protocols. devices, mechanisms, systems, and methods described herein.

For example, when the present disclosure states that a method or device performs task "X" (or that task "X" is performed), such a statement should be understood to disclose that processing system 500 can be configured to perform task "X". Processing system 500 is configured to perform a function, method, or operation at least when processors 502 are configured to do the same.

Memory 504 can include volatile memory, non-volatile memory, and any other medium capable of storing data. Each of the volatile memory, non-volatile memory, and any other type of memory can include multiple different memory devices, located at multiple distinct locations and each having a different structure. Memory 504 can include remotely hosted (e.g., cloud) storage.

Examples of memory 504 include a non-transitory computer-readable media such as RAM, ROM, flash memory, EEPROM, any kind of optical storage disk such as a DVD, a Blu-Ray® disc, magnetic storage, holographic storage, a HDD, a SSD, any medium that can be used to store program code in the form of instructions or data structures, and the like. Any and all of the methods, functions, and operations described herein can be fully embodied in the form of tangible and/or non-transitory machine-readable code (e.g., interpretable scripts) saved in memory 504.

Input-output devices 506 can include any component for trafficking data such as ports, antennas (i.e., transceivers), printed conductive paths, and the like. Input-output devices 506 can enable wired communication via USB®, Display-Port®, HDMI®, Ethernet, and the like. Input-output devices 506 can enable electronic, optical, magnetic, and holographic, communication with suitable memory 506. Input-output devices 506 can enable wireless communication via WiFi®, Bluetooth®, cellular (e.g., LTE®, CDMA®, GSM®, WiMax®, NFC®), GPS, and the like. Input-output devices 506 can include wired and/or wireless communication pathways.

Sensors 508 can capture physical measurements of environment and report the same to processors 502. User interface 510 can include displays, physical buttons, speakers, microphones, keyboards, and the like. Actuators 512 can enable processors 502 to control mechanical forces.

Processing system 500 can be distributed. For example, some components of processing system 500 can reside in a remote hosted network service (e.g., a cloud computing environment) while other components of processing system 500 can reside in a local computing system. Processing system 500 can have a modular design where certain modules include a plurality of the features/functions shown in FIG. 5. For example, I/O modules can include volatile memory and one or more processors. As another example, individual processor modules can include read-only-memory and/or local caches.

FIG. 6 illustrates a process for privacy preservation according to an embodiment of the present disclosure. For instance, at block 602, a computing entity (e.g., the server 104) determines (e.g., selects), based on public randomness (e.g., from a random beacon service 106), a set of super-clients (e.g., super-clients 108).

At block 604, the computing entity obtains, from a plurality of client devices (e.g., clients 102), a plurality of masked inputs. For instance, each client (e.g., each client device) can send random values to the set of super-clients determined at block 602. The random values are used to mask the client private input. Then, the clients can send the masked input also to the computing entity.

At block 606, the computing entity obtains, from each of the set of super-clients, aggregated random values received by the super-client from the other clients.

At block 608, the computing entity aggregates the plurality of masked inputs received from the plurality of client devices and the aggregated random values from the set of super-clients.

In the following, several embodiments of the present invention using the secure aggregation protocols with public randomness are discussed. For instance, in some embodiments, blinding (e.g., secret-sharing) is used. In other embodiments, homomorphic encryption is used. In some variations, the secure aggregation protocols can take several rounds and clients can go offline at any time.

For blinding, a random beacon service (e.g., random beacon service 106) is provided that broadcasts unbiased random seeds either on demand or at pre-defined time intervals. A Public Key Infrastructure (PKI) is also provided that distributes authentic public keys of clients (e.g., the users of system 100) and/or the server 104.

$\mathcal{U}$ denotes the initial set of clients, and $|\mathcal{U}|$=n. For example, $\mathcal{U}$ denotes the clients such as all of the users of system 100. The size of $\mathcal{U}$ i.e., the total number of clients in system 100, is denoted by n.

In a first step, the server 104 obtains the public keys of all clients from the PKI and receives the random seed Q from the random beacon service 106. For instance, the server 104 obtains the public keys from the users (e.g., users 104A-104E) of system 100 and public randomness (e.g., the random seed Q) from the random beacon service 106. The server 104 computes the set of super-clients $\mathcal{K} \leftarrow \{i : F(Q; pk_i) < \tau\}$ by evaluating a PRF F keyed with the random seed Q, where $\tau$ is a protocol parameter. For example, the server 104 determines (e.g., calculates, computes, and/or obtains) a set of super-clients, $\mathcal{K}$, based on a PRF, F. For instance, the server 104 inputs (e.g., keys) a random seed, Q, with the public keys, $pk_i$, from the clients into the PRF to determine the set of super-clients. Furthermore, the server 104 uses a protocol parameter, $\tau$, to determine the set of super-clients.

For example, if the range of F is [0,1] (e.g., the output from the PRF is between 0 and 1), the server 104 can set $\tau$ to 0.1 so to have clients be appointed super-client with 0.1 probability. For instance, if there are 100 total users (e.g., clients) in the system 100 and the protocol parameter is 0.1, then the server 104 may determine 10 clients as super-clients.

For each super-client $i \in \mathcal{K}$ (e.g., each super-client i that is an element of the total set of super-clients $\mathcal{K}$), the server 104 can also compute the list of backup clients $\mathcal{L}_i = \{G_B(Q, pk_i, j)\}_{1 < j < l}$ using a Pseudo-random Generator (PRG) $G_B$ and encoding the PRG output as a list of l clients. The PRG range is [n], which is the set itself (e.g., the set $\{1, 2, \ldots, n-1, n\}$). For instance, the server 104 determines the list of backup clients, $\mathcal{L}_i$, using a PRG, $G_B$. For example, the server 104 inputs the random seed Q, the public keys, $pk_i$, and j. As used herein, "i" and "j" refer to users (e.g., the clients 102), which can include a regular user, a super-client, and/or a backup client. Further, as used herein, it should be understood that the user "i" and/or the user "j" might not refer to the same user from a preceding section and/or embodiment (e.g., the user "i" may refer to multiple different users in different sections such as a super-client in one section and a backup client in another). In most embodiments, the first user may be designated "i" and additional users may be designated "j". In other embodiments, this may be reversed.

In a second step, the super-clients obtain the public keys of every user from the PKI. For instance, the server 104 can provide an indication to the users of the system 100 that have been determined as super-clients. Then, the super-clients can request and obtain the public keys from the users of the system 100. Further, each super-client i from the entire list of super-clients, $\mathcal{K}$, determines (e.g., computes and/or obtains) the list of its backup clients $\mathcal{L}_i$. For example, both the server 104 and the super-clients may become aware of the list of backup clients for that super-user by determining the list of its backup clients. In some instances, the server 104 computes this list and sends it to the super-client. In other instances, the server 104 and the super-client compute this list individually. The list can be determined by randomness Q, and both parties can end up with the same list in both instances. Each super-client i secret-shares its secret key $sk_i$ in a $t_s$ out of l scheme, creating shares $\{sk_{ij}\}_{j \in \mathcal{L}_i}$, where $l = |\mathcal{L}_i|$ and $t_s$ is a tunable parameter determining the number of shares required to reconstruct $sk_i$. For instance, the shares may be determined using a Shamir secret-sharing. For example, the entity (e.g., the super-client) computing the shares of the secret S may draw a random polynomial (e.g., "f(x)") of degree t−1 such that f(0)=S. Next, the same party computes the i-th share as f(i). Given t or more shares (e.g., t is the tunable parameter), f(0) can be recovered, that is the secret S, via interpolation. In operation, each super-client i shares its secret key, $sk_i$, with its backup clients. For example, for five total backup clients (e.g., l is five from the list of backup clients $\mathcal{L}_i$), the super-client can determine that three (e.g., $t_s$ is three) can be used to reconstruct the super-client's secret key. The super-client can provide shares of its key to the back-up neighbors such that only three of them are needed to reconstruct the secret key $sk_{ij}$.

For instance, for each backup client j, the super-client i can encrypt share $sk_{ij}$ under the public key of backup client j and send the ciphertext to backup client j. For example, using the public key of the backup client, the super-client encrypts its secret key $sk_{ij}$, and provides the encrypted secret key (e.g., ciphertext) to the backup client.

In a third step, each client i generates k masking seeds $\{b_{ij}\}_{j \in \mathcal{K}}$, one for each super-client $j \in \mathcal{K}$. The masking seeds may be drawn randomly (e.g., the masking seeds may be a random value in the domain of function G, which is a PRG). For instance, each client generates a number of masking seeds, where k represents the total number and $b_{ij}$ represents the masking seeds that are generated. Then, for each super-client j, client i encrypts seed $b_{ij}$ under the public key of super-client j and sends the ciphertext to super-client j. For instance, the client encrypts its masking seed for a particular super-client with the public key of the super-client, and provides the encrypted masking seed (e.g., ciphertext) to that super-client. Next, the client i computes $y_i = x_i + B_i$, where $B_i = \sum_{j \in \mathcal{K}} G(b_{ij})$ and G is a PRG, and sends it to the server. For example, the client may compute $B_i$, which is computed as the sum of the outputs of G evaluated at all $b_{ij}$. For instance, if the entity computing this sum is a first client and nodes 3, 7, 8 are super-clients (e.g., clients 3, 7, and 8 are super-clients), then node 1 (e.g., the first client) may draw three masking seeds: b_13, b_17, b_18. Hence, B_1=G(b_13)+G(b_17)+G(b_18). In some variations, the client determines the masked input $y_i$ based on the private input $x_i$ and randomly drawn information $B_i$. For instance, the client determines the randomly drawn information by using a summation function for each of the super-clients within the total set of super-clients and a PRG, G, with the generated masked seeds for each of the super-clients.

In a fourth step, which can be performed if the third step above is performed (e.g., based one or more of the clients dropping out that is described above), denote $U_2 \subseteq U_1$ as the set of clients that completed step three above. For instance, $U_2$ is a subset of $U_1$, which includes the total number of clients in system 100, and $U_2$ is the set of clients that completed the third step above. For this subset, the super-clients receive the masking seeds from these clients within the subset. Then, the super-client j computes $$B_j^{sum} = \sum_{i \in U_2} G(b_{ij})$$

and sends $$B_j^{sum}$$

to the server 104.

$$B_j^{sum}$$

may be computed similarly to $B_i$, which is described above.

$$B_j^{sum}$$

is the aggregated random value from the other clients (e.g., clients other than the super-client that computes the aggregated random value). Each super-client can send the aggregated random value to the server 104 such that the server obtains a plurality of aggregated random values.

Next, denote $\mathcal{K}_1 \subseteq \mathcal{K}$ as the set of super-clients that completed step four above. Let $r=|\mathcal{K}_1|$. For instance, $\mathcal{K}_1$ is a subset of the total super-clients $\mathcal{K}$ that completed step four above, and r is the number (e.g., amount) of the subset of super-clients.

In some examples, if r<k, then a fifth step is carried out. For instance, if the number from the subset of super-clients that completed step four is less than k, then a fifth step is carried out. "k" is the size of the set of super-clients, and is a tunable parameter. In a fifth step, the server 104 sends the list of dropout super-clients $\mathcal{K} \setminus \mathcal{K}_1$ to all neighbors of all super-clients $\{\mathcal{L}_i\}_{i \in \mathcal{K}}$. For instance, "\" represents the set difference formed by all of the super-clients that are not within the subset of super-clients $\mathcal{K}_1$. The server 104 sends the list of these super-clients that are not within the subset of super-clients above to the backup clients $\mathcal{L}_i$ for the super-clients. Each backup client j of dropped super-client i decrypts and sends to the server their share of super-client i's secret key $sk_{ij}$. For each dropped super-client i, if the server 104 receives at least $t_s$ shares of the secret key, the server 104 reconstructs the secret key $sk_i$ of the dropped out super-client. The set of super-clients from which the secret key has been reconstructed can be denoted as $\mathcal{K}_{rec}$. Then, let $r_d=|\mathcal{K}_{rec}|$ (e.g., $r_d$ is the magnitude of $\mathcal{K}_{rec}$). The server 104 then decrypts and obtains the blinding seeds sent to dropped super-client i: $\{b_{ji}\}_{j \in U_2}$. The server gets (e.g., obtains)

$$B_i^{sum}$$

for each super-clients $i \in \mathcal{K}_{rec}$.

In some instances, if r is at least k (e.g., r is greater than or equal to k) or $r+r_d$ is at least k (e.g., $r+r_d$ is greater than or equal to k), then a sixth step is carried out. In the sixth step, the server 104 determines (e.g., computes) the sum of blindings as $$\sum_{i \in U_2} B_i = \sum_{j \in \mathcal{K}} B_j^{sum},$$

and outputs $\sum_{i \in U_2} x_i = \sum_{i \in U_2} y_i - \sum_{i \in U_2} B_i$.

In some embodiments of the present invention, homomorphic encryption is used. For instance, compared to the embodiments using blinding, an additively homomorphic encryption scheme and a public key PK for the set of super-clients are provided such that each super-client holds a share of the corresponding decryption key. In these embodiments, the first two steps (e.g., steps one and two) described above with the use of blinding are the same and are not repeated for brevity.

At a third step, each client i encrypts its input $x_i$ under the super-clients public key PK and sends the ciphertext, denoted it as $y_i$, to the server 104. For instance, the server 104 obtains the ciphertext (e.g., the encrypted input) that is encrypted based on the clients private input $x_i$ and the super-clients public key PK.

Next, denote $U_2 \subseteq U_1$ as the set of clients that completed step three above. For instance, $U_2$ is a subset of $U_1$, which includes the total number of clients in system 100, and $U_2$ is the set of clients that completed the third step above. In step four, the server 104 aggregates all ciphertexts received from clients in $U_2$ as $ysum=\sum_{i \in U_2} y_i$ and provides $y_{sum}$ to the super-clients. For instance, the server 104 determines, from the masked inputs from the clients $y_i$, an aggregation (e.g., by using a summation $\Sigma_{i \in U_2} y_i$ of the clients i within the set $U_2$) of the masked inputs, which is denoted by ysum.

At step five, each super-client uses its share of the decryption key to partially decrypt $y_{sum}$ and sends the partially decrypted ciphertext to the server 104. The decryption key might not be public, but may be tied (e.g., associated with) the public key.

Following, denote $\mathcal{K}_1 \in \mathcal{K}$ as the set of super-clients that completed step five above. Let $r = |\mathcal{K}_1|$. For instance, $\mathcal{K}_1$ is a subset of the total super-clients $\mathcal{K}$ that completed step five above, and r is the number (e.g., amount) of the subset of super-clients.

If r<k, then step six is performed. For instance, if the number from the subset of super-clients that completed step four is less than k, then a sixth step is carried out. For instance, step six, the server 104 sends the list of dropout super-clients $\mathcal{K} \setminus \mathcal{K}_1$ to all neighbors of all super-clients $\{\mathcal{L}_i\}_{i \in \mathcal{K}}$. For instance, \ represents the set difference formed by all of the super-clients that are not within the subset of super-clients $\mathcal{K}_1$. The server 104 sends the list of these super-clients that are not within the subset of super-clients above to the backup clients $\mathcal{L}_i$ for the super-clients. Each backup client j of dropped super-client i decrypts and sends to the server 104 their share of super-client i's secret key $sk_{ij}$. For each dropped super-client i, if the server receives at least $t_s$ shares of the secret key, the server 104 reconstructs the secret key $sk_i$. The set of super-clients from which the secret key has been reconstructed can be denoted as $\mathcal{K}_{rec}$. Then, let $r_d = |\mathcal{K}_{rec}|$ (e.g., ra is the magnitude of $\mathcal{K}_{rec}$). The server can thus carry out the partial decryption of $y_{sum}$ (e.g., the aggregation of the masked inputs) on behalf of each super-client in $\mathcal{K}_{rec}$.

If $r+r_d=k$, then step seven is performed. In step seven, the server 104 can decrypt $y_{sum}$ and obtain $\Sigma_{i \in U_2} x_i$. For instance, $\Sigma_{i \in U_2} x_i$ is the sum of the individual inputs from all of the users.

Embodiments of the present invention provide for the following improvements and advantages over existing computer systems and computer networks specially adapted and programmed for aggregation:

1. Masking, by a client of a distributed application, a client input with a set of client-drawn random values and sending, by the client, the masked input to the server, and sending, by the client, each of the client-drawn random values to a set of selected super-clients, chosen by means of public randomness.
2. Adding, by each of the selected super-clients, the random values received from the other clients and sending the result to the server
3. Adding, by the server, the masked inputs received from clients and the sum of random values received from the selected super-clients so as to compute the sum of the client inputs.
4. Providing for low communication overhead in terms of total number of messages and in terms of average number of messages per client, thereby enabling to save computational power, computation time and/or computational resources to perform the aggregations, while also decreasing the load on the computer network.

In an embodiment, the present invention provides a method for single-server secure aggregation comprising the steps of:

1. Selecting, by means of public randomness, a set of super-clients.
2. Sending, by each client, random values to the set of selected super-clients of step 1 and using the random values to mask the client private input.
3. Sending, by each client, the masked input to the server.
4. Sending, by each selected super-client of step 1, the sum of the random values received by the other clients to the server. For instance, the super-client j may send a message to the server. For the blind use embodiment(s) described above, the message is $$B_j^{sum}.$$

For the homomorphic encryption embodiment(s), the message is a partially decrypted $y_{sum}$.

5. Adding, by the server, the masked inputs received by the clients and the aggregated random values received by the selected super-clients of step 1. For instance, note that $$\sum_{i \in U_2} B_i = \sum_{j \in \mathcal{K}} B_j^{sum}.$$

Hence, 
$$\sum_{i \in U_2} y_i - \sum_{j \in \mathcal{K}} B_j^{sum} = \sum_{i \in U_2} x_i + \sum_{i \in U_2} B_i - \sum_{j \in \mathcal{K}} B_j^{sum} =$$
$$\sum_{i \in U_2} x_i + \sum_{i \in U_2} B_i - \sum_{i \in U_2} B_i = \sum_{i \in U_2} x_i.$$

For instance, each client may mask their input with one random value per super-client and share each of those random values with each of the super-clients. The sum of user inputs may thus include a random value per client per super-client. Each super-client adds the random values it gets from each client and sends it to the server. The sum of the random values (e.g., $$B_j^{sum}$$

and/or $y_{sum}$) at the server 104 is the sum of each random value per client per super-client. Hence, the two quantities cancel out and the server 104 determines (e.g., learns) the sum of the individual inputs.

Embodiments of the present invention thus provide for general improvements to computers in machine learning systems to provide for integrity verification for secure aggregation by a server. Moreover, embodiments of the present invention can be practically applied to use cases to effect further improvements in a number of technical fields including, but not limited to, medical (e.g., digital medicine, personalized healthcare, AI-assisted drug or vaccine development (AIDD or Oncoimmunity), etc.) and smart cities (e.g., automated traffic or vehicle control, smart districts, smart buildings, smart industrial plants, smart agriculture, energy management, etc.), forecasting, and in particular any application that would benefit from secure aggregation.

In the following, further background and description of exemplary embodiments of the present invention, which may overlap with some of the information provided above, are provided in further detail. To the extent the terminology used to describe the following embodiments may differ from the terminology used to describe the preceding embodiments, a person having skill in the art would understand that certain terms correspond to one another in the different embodiments. For example, herein, clients may also be referred to as users, super-clients can be referred to as committee members, and the private inputs of the clients provided to the server may also be referred to as hidden, noisy, blinded or masked. Features described below can be combined with features described above in various embodiments.

Secure aggregation can be a key component of privacy-friendly federated learning applications, where the server learns the sum of many user-supplied gradients, while individual gradients are kept private. State-of-the-art SA protocols can protect individual inputs with zero-sum random shares that are distributed across users, have a per-user overhead that is logarithmic in the number of users, and take more than 5 rounds of interaction.

An example embodiment of the present invention provides LIghtweight Secure Aggregation (LiSA), an SA protocol that leverages a source of public randomness to minimize per-user overhead and the number of rounds. In particular, LiSA can use two rounds and has a communication overhead that is asymptotically equal to that of a non-private protocol—one where inputs are provided to the server in the clear—for most of the users. The example embodiment of LiSA can use the public randomness to select a subset of the users—a committee of super-clients—that aid the server to recover the aggregated input. Users blind their individual inputs with random values shared with each of the super-clients, and each super-client provides the server with an aggregate of the randomness shared with each user. It can be possible that when one super-client is honest, the server cannot learn individual inputs but only the sum of threshold-many inputs.

Secure aggregation allows a set of parties to compute a linear function (e.g., the sum) of their inputs while keeping each party's input private. Recently, secure-aggregation protocols have been proposed as a privacy-preserving mechanism for federated learning. where a large number of users and a central server train a joint model by leveraging user-private gradients.

Secure aggregation requires users to provide a noisy version of their inputs to the server so that, when all noisy inputs are aggregated, the noise cancels-out and the server learns the aggregated gradient. An SA protocol can minimize the overhead at the user and the number of rounds, since in many federated learning applications, users are devices with limited computing power and an erratic online behavior. This can be, for example, the case of federated learning used to train voice recognition or text prediction models on mobile phones.

For instance, when assuming the availability of a random beacon service, e.g., a source of public randomness, efficient secure aggregation protocols for federated learning can be designed. LiSA is a secure aggregation protocol that leverages a public random beacon to minimize overhead. For example, LiSA can protect user inputs with random noise. Thus, LiSA uses the random beacon at each learning epoch to select a small subset of the users, namely a committee of super-clients, that hold the seeds necessary to remove the noise from the inputs provided by the users. The technique used to add and remove noise from the inputs can be such that as long as one super-client is honest, a compromised server cannot learn individual user inputs but only the sum of threshold many inputs. The random choice of super-clients ensures (with a high probability) that at least one super-client is honest, despite that a fraction of the users may be compromised. Users of LiSA can add noise to their inputs with randomness derived from a non-interactive key agreement with each of the super-clients. Hence, super-clients can provide the server with the same aggregated randomness added by the clients, so that the aggregated inputs can be de-noised. In order to protect individual user inputs, honest super-clients must not share with the server the noise used to blind an individual input, but rather provide the server with aggregated noise, so that the server can de-noise only aggregated inputs. LiSA further uses the random beacon to select, for each super-client, a set of backup clients uniformly at random. The backup clients of a super-client allow the server to recover the aggregated randomness, shared by the users with the super-client, in the event that the super-client may go offline (e.g., due to network outages, system failure, or adversarial compromise).

Formally, with a single server S and set of n users $\mathcal{U}$, without loss of generality, each user can be identified with a member of [n] so that $\mathcal{U}=[n]$. User $i \in \mathcal{U}$ holds private input x . The protocol should allow the server to learn y= $\sum_{i \in \mathcal{U}} x_i$. Users have no direct communication channels as all messages are routed through the server. A PKI distribute the genuine user public keys. Hence any pair of users establish a confidential and authenticated channel. Further, each user have a confidential and authenticated channel with the server. Protocols be designed that are robust—that is, protocols that provide the aggregation output—in presence of a $\delta$ fraction of users that go offline at any time during the protocol execution.

Semi-honest as well as malicious settings can be accounted for. In the semi-honest settings, corrupted parties can follow the protocol as expected; in the malicious settings, corrupted parties can act arbitrarily. In both cases, the adversary can corrupt the server and a $\gamma$ fraction of the users, statically. The security of the protocols can guarantee that the input of an honest user is aggregated with at least an a fraction of all other inputs before it is revealed to the server in the clear. In other words, the server learns y=$\sum_{i \in \mathcal{U}'} x_i$ if $\mathcal{U}' \subseteq \mathcal{U}$ and $|\mathcal{U}'| \geq \alpha n$. Denials of services attacks or attacks to the integrity of the computation may considered via other protocols. The notations are provided in Table 1 below.

TABLE 1

| Frequently used notations. | |
| --- | --- |
| Symbol | Description |
| System model | |
| $\mathcal{U}$ | Set of clients |
| $\mathcal{D}$ | Set of dropout users |
| $\mathcal{C}$ | Set of corrupt clients |
| n | Overall number of clients |
| $\delta$ | Fraction of dropped clients |
| $\gamma$ | Fraction of corrupt clients |
| Q | Public randomness |
| Protocol parameters | |
| $\mathcal{K}$ | Committee of super-clients |
| $\mathcal{L}_j$ | Backup clients set for super-client j |
| k | Size of the set of super-clients, $k \leq n$ |
| $\ell$ | Size of backup-clients sets, $\ell \leq n$ |
| t | Secret sharing reconstruction threshold, $t \leq \ell$ |
| $\tilde{c}$ | Estimated number of corruptions in $\mathcal{K}$ |
| $\alpha$ | Minimum fraction of aggregated inputs |

A specification of a semi-honest protocol is provided in process 1, with changes that can be made to the semi-honest protocol so as to withstand a malicious server, as discussed below. In a protocol, each user can assume up to three roles: regular user, super-client, and backup-client. Each user $i \in \mathcal{U}$ can have two key-pairs $(sk_i, pk_i)$ $(SK_i, PK_i)$ used for non-interactive key agreement. Key pair $(SK_i, PK_i)$ can be used by user i when she acts as a super-client, whereas key-pair $(sk_i, pk_i)$ can be used for all other purposes.

During round 1, all users and the server can use the random beacon to select a committee of super-clients, denoted as $\mathcal{K}$, at random. In particular, $\mathcal{K} \leftarrow$ Select(Q, $\mathcal{U}$,k) denotes a function that selects k users from $\mathcal{U}$ by means of a PRG seeded with randomness Q.

During round 2, each user i can add noise to her input $x_i$ by using k random masks, each shared with one of the super-clients. In particular, user i can agree on a shared key with super-client j by running $$k_{i,j}^* = KA. \text{ Agree}(sk_i, PK_j)$$

and then obtain a mask as $$F(k_{i,j}^*),$$

where F is a PRG. The noisy input, denoted as $c_i$, is sent to the server.

The server can aggregate the noisy inputs as $c_{agg}$, and asks each of the super-clients for the aggregated randomness required to de-noise $c_{agg}$ (round 3). When $$\mathcal{U}_1'$$

is the set of users from who the server receives a noisy input, each super-client j runs a non-interactive key agreement with each user $$i \in \mathcal{U}_1'$$

to obtain $$\{k_{j,i}^* = KA. \text{ Agree}(SK_j, pk_i)\}_{i \in \mathcal{U}_1'}.$$

Next, super-client j can use each of the agreed keys to obtain the shared masks by means of a PRF, aggregate all the shared masks as $\partial_j$, and send it to the server. Finally, the server can obtain the aggregated masks from each super-client and subtracts those to $c_{agg}$ to remove the noise and obtain the aggregated output.

The above protocol might not be robust against dropouts by super-clients. For example, when a user $j \in \mathcal{K}$ goes offline before she sends her aggregated noise share $\partial_j$ to the server (round 3, step 6), then the aggregated noisy input might no longer be de-noised. Robustness can be added by selecting a set $\mathcal{L}_j$ of $\ell$ backup clients for each super-client j, and by asking j to secret-share her secret key $SK_j$ among them, with reconstruction threshold $t \leq \ell$ (round 2).

Similar to the committee selection, the selection of a backup set can use the randomness provided by the random beacon service. In this case, each super-client j runs $\mathcal{L}_j \leftarrow$ Select(Q||j, $\mathcal{U}$,l) to select l backup clients. The PRG of the Select function can be seeded with Q||j—the random beacon Q concatenated with the index of the super-client j—so that different super-clients obtain independent sets of backup clients.

If a super-client j goes offline before she can send the aggregated noise share, the server can recover j's secret key by asking for her shares to her backup clients (round 4). If t—many users in j's backup set $\mathcal{L}_j$ send a share of $SK_j$ to the server (round 5), then the server can recover the key and compute the aggregated noise share (round 6), despite j being offline.

Backup clients can aid the server in recovering the secret key of a super-client if the number of dropped-out super-clients $|\mathcal{K}_{drop}|$ is below k−č, where č is the expected number of super-clients that are corrupted. This can make sure that even by corrupting some super-clients and by recovering some secret keys via backup clients, the server may still be missing at least one secret key of a super-client and, therefore, cannot de-noise individual noisy inputs of victim users.

Regular users may need to be online until round 2, then they can go offline. Super-clients and backup clients may be required to remain online until round 3 and until round 5, respectively.

Also, in the example of process 1, each user encrypts a single message to ease readability. In case users encrypt vectors of size m, each element can be encrypted separately, and aggregation can be carried-out element-wise.

The malicious protocol can follow the same blueprint of the semi-honest one. Differences between the two protocol can stem from the ability of a corrupted server to act arbitrarily. Steps 3 and 4 of round 4 of process 1, and steps 1-4 of round 5 of process 1, provide changes that can be made to the semi-honest protocol so as to withstand a malicious server.

A malicious server can declare different sets of dropped-out super-clients, each of size <k−č, to different backup sets, so to obtain their key-shares. When the server manages to obtain the secret keys of each honest super-client, it can remove noise from any single noisy input, thereby breaking security. Round 4 and round 5 can be used to run a consistency check among backup sets, so as to agree on the set of dropped-out super-clients; if the size of this set is bigger than a threshold.

Process 1: LiSA secure aggregation protocol with input privacy. Parties: Server and users $\mathcal{U}$=[n]. Public parameters: input domain $\mathbb{X}$, fraction of drop-outs δ, fraction of corruptions γ, security parameter for cryptographic primitives λ, committee size k, backup-set size l, secret sharing reconstruction threshold t, minimum fraction of aggregated inputs α, maximum number of corrupt super-clients č. Prerequisites: Each user $i \in \mathcal{U}$ has key-pairs computed as $$(sk_i, pk_i) \leftarrow KA. \text{ Gen}(1^\lambda),$$

$$(SK_i, PK_i) \leftarrow KA. \text{ Gen}(1^\lambda) \text{ and } (sk_i^s, pk_i^s) \leftarrow DS. \text{ Gen}(1^\lambda);$$

$$\text{public keys } (pk_i, PK_i, pk_i^s)$$

are registered with the PKI.

For $\mathcal{U}$ and $r \in [6]$, the set of users that complete the execution of round r without dropping out are denoted by $\mathcal{U}_r$, and the set of users the server knows have completed round r are denoted by $$\mathcal{U}'_r.$$

It holds $$\mathcal{U}'_r \subseteq U_r \subseteq \mathcal{U}_{r-1}$$

for all $r \in [6]$.

Round 1: each party (1) receives random seed Q; and (2) selects committee $\mathcal{K} \leftarrow \text{Select}(Q, \mathcal{U}, k)$.

Round 2: a super-client $j \in \mathcal{K}$ (1) selects backup sets $\mathcal{L}_j \leftarrow \text{Select}(Q\|j, \mathcal{U}\backslash\{j\}, \ell)$; (2) fetches public keys of backup clients $\{pk_i\}_{i\in\mathcal{L}_j}$ from the PKI; (3) derives symmetric keys:

$$\left\{k^e_{j,i} \leftarrow KA(\text{"ENC"}; sk_j, pk_i)_{i\in\mathcal{L}_j}\right;$$

(4) secret shares key $SK_j$: $\{S_{j,i}\}_{i\in\mathcal{L}_j} \leftarrow \text{SS.Share}(\ell; t; SK_j)$; (5) encrypts shares of $$SK_j : \left\{E_{j,i} \leftarrow AE.\ Enc(k^e_{j,i}, S_{j,i})\right\}_{i\in\mathcal{L}_j};$$

and (6) sends $\{(j; i; E_{j,i})\}_{i\in\mathcal{L}_j}$ to the server. User $i \in \mathcal{U}$ (1) fetches public keys $\{PK_j\}_{j\in\mathcal{K}}$ from the PKI; (2) derives symmetric keys:

$$\left\{k^*_{i,j} \leftarrow KA(PRG; sk_i, PK_j)\right\}_{j\in\mathcal{K}};$$

(3) computes blinded input:

$$c_i \leftarrow x_i + \sum_{j\in\mathcal{K}} F(k^*_{i,j});$$

and (4) sends $c_i$ to the server.

Round 3: a server (1) receives encrypted key shares $\{(j; i; E_{j,i})\}_{i\in\mathcal{L}_j}$ from $j \in \mathcal{K} \cap$ $$\mathcal{U}'_2$$

and sends each of them to a corresponding backup client; (2) receives blinded inputs $c_i$ from users $$i \in \mathcal{U}'_2;$$

(3) aggregates input $c_{agg} \leftarrow \Sigma_{i\in\mathcal{U}'_2} c_i$; (4) sends $$\mathcal{U}'_2$$

to super-clients $j \in \mathcal{K} \cap$ $$\mathcal{U}'_2.$$

A super-client $$j \in \mathcal{K} \cap \mathcal{U}'_2 \qquad\qquad (1)$$

receives $$\mathcal{U}'_2$$

from the server; (2) if $$|\mathcal{U}'_2| < \alpha n,$$

aborts; (3) fetches public keys $\{pk_i\}_{i\in\mathcal{U}'_2}$ from the PKI; (4) derives symmetric keys $$\left\{k^*_{j,i}\right) \leftarrow KA(\text{"PRG"}; SK_j, pk_i)\right\}_{i\in\mathcal{U}'_2};$$

(5) computes partial blinding $\partial_j \leftarrow \Sigma_{i\in\mathcal{U}'_2}$ $$F(k^*_{j,i});$$

and (6) sends $\partial_j$ to the server.

Round 4: a server, when $$// \mathcal{K}_{alive} := \mathcal{K} \cap \mathcal{U}'_3 \text{ and } \mathcal{K}_{drop} := \mathcal{K}\backslash\mathcal{K}_{alive}$$

and $\mathcal{L} = \cup_{j\in\mathcal{K}} \mathcal{L}_j$, (1) receives $\{\partial_j\}_{j\in\mathcal{K}_{alive}}$ from super-clients in $\mathcal{K}_{alive}$; (2) if $|\mathcal{K}_{alive}|=k$ jumps to step (2) of Round 6; and (3) sends $\mathcal{K}_{drop}$ to all users in $\mathcal{L}$. A backup client $i \in \mathcal{L}$ (1) receives $\mathcal{K}_{drop}$ from the server; (2) if $|\mathcal{K}_{drop}|\geq k-\tilde{c}$, then aborts; (3) computes signature $$\sigma_i \leftarrow DS.\ \text{Sign}(sk^s_i; \mathcal{K}_{drop});$$

and (4) sends $\sigma_i$ to the server.

Round 5: a server (1) receives $\{\sigma_i\}_{i\in\mathcal{L}\cap\mathcal{U}'_3}$ from users $\mathcal{L} \cap \mathcal{U}'_3$ and forwards them to all users in $\mathcal{L}\cap\mathcal{U}'_3$. A backup client $i \in \mathcal{L}\cap\mathcal{U}'_3$ (1) receives $\{\sigma_i\}_{i\in\mathcal{L}\cap\mathcal{U}'_3}$; (2) fetches $\{pk^s_i\}_{i\in\mathcal{L}\cap\mathcal{U}'_3}$ from the PKI; (3) computes $\mathcal{L}_{ack}=\{l\in(\mathcal{L}\cap\mathcal{U}'_4: DS.\ \text{Verif}(pk^s_i; \sigma_i; \mathcal{K}_{drop})=\text{TRUE}\}$; (4) if $|\mathcal{L}_j\cap$ $\mathcal{L}_{ack}| \lt t$ for any $j \in \mathcal{K}$, then aborts; and (5) for any $j \in \mathcal{K}_{drop}$ such that $i \in \mathcal{L}_j$: (a) fetches $pk_j$ from the PKI; (b) derives symmetric key $$\left(k_{i,j}^e\right) \leftarrow KA\left(\text{``ENC''}; sk_i, pk_j\right);$$

(c) decrypts $$S_{j,i} \leftarrow AE.\ Dec\left(k_{i,j}^e; E_{j,i}\right)$$

and (d) sends $S_{j,i}$ to the server.

Round 6: a server (1) for each $j \in \mathcal{K}_{drop}$: (a) collects shares $\{S_{j,i}\}_{i \in \mathcal{L}_j \cap \mathcal{U}_5'}$ and aborts if the server receives less than t shares; (b) reconstructs secret key $SK_j \leftarrow SS.Rec$ $(\{S_{j,i}\}_{i \in \mathcal{L}_i \cap \mathcal{U}_5'})$; (c) derives symmetric keys $$\left\{k_{j,i}^s \leftarrow KA(PRG; SK_j; pk_i)\right\}_{i \in \mathcal{U}_2'};$$

and (d) computes missing partial blinding $$\partial_j' \leftarrow \Sigma_{i \in \mathcal{U}_2'} F\left(k_{i,j}^s\right);$$

and (2) given $\{\partial_j\}_{j \in \mathcal{K}} = \{\partial_j\}_{j \in \mathcal{K}_{alive}} \cup \{\partial_j\}_{j \in \mathcal{K}_{drop}}$, computes the output: $y \leftarrow c_{agg} \Sigma_{j \in \mathcal{K}} \partial j$.

When $k - \tilde{c}$, then it is possible that no honest backup client will help the server in recovering the missing keys.

Adding integrity protection to LiSA: LiSA can guarantee input privacy, and may treat attacks against the integrity of the aggregation as out of scope. The following example (e.g., process 2) adds an integrity protection mechanism to LiSA.

A commitment scheme (COMM.Gen,COMM.Vfy) can be hiding and binding. In particular, given a message m and randomness r, comm←COMM.Gen(m, r) is a commitment to message m; opening the commitment requires revealing both m and r. To verify whether m, r is a valid opening for comm, one can run COMM.Vfy(comm, m,r) that provides a TRUE/FALSE output. The commitment scheme can be linearly-homomorphic. That is, given $comm_1 \leftarrow COMM.Gen$ $(m_1, r_1)$ and $comm_2 \leftarrow COMM.Gen(m_2, r_2)$, there is a "multiplication" operation $\odot$ such that $comm_1 \odot$ comm2$==$COMM.Gen$(m_1+m_2, r_1+r_2)$. In other words COMM.Vfy(comm$_1 \odot$comm$_2$, $m_1+m_2, r_1+r_2$) outputs TRUE. Pedersen commitments can also fulfill the above properties. The details of an embodiment of the protocol are shown in process 2 through 6 example rounds and steps. For instance, each user i can commit to her input $x_i$ with randomness $r_i$ and send the commitment comm$_i$ to all of the super-clients. Hence each super-client j can multiply the commitments received from the server so as to obtain a commitment to the sum of the inputs, say $C_j = \odot_{i \in \mathcal{U}} comm_i$. Each super-client can publish $C_j$ and the protocol can abort as soon as one of the published $C_j$ differs from the others. As long as one super-client is honest, it can be ensured that (i) the server provides the same set of commitments to the super-clients, and (ii) that all super-clients publish the same $C_j$; if one of those conditions does not hold, the protocol can be aborted. Note that $C_j$ is a commitment to $y \Sigma_{i \in \mathcal{U}} x^i$ with randomness $r \Sigma_{i \in \mathcal{U}} r_i$.

At the same time, each client i can secret-share the randomness $r_i$ used to create comm$_i$ across all of the super-clients. Hence, super-client j receives $r_{i,j}$ such that $r_i = \Sigma_{j \in \mathcal{K}} r_{i,j}$; as long as one super-client is honest, $r_i$ is not leaked to the adversary and commitment comm$_i$ does not leak $x_i$.

Further, each super-client can compute and publish the sum of received random shares. That is, super-client j publishes $\rho_j = \Sigma_{i \in \mathcal{U}} r_{i,j}$, where $\Sigma_{j \in \mathcal{K}} \rho_j == \Sigma_{i \in \mathcal{U}} r_i$. Hence, when the server publishes the aggregate sum y, a client can accept it as valid if COMM.Vfy($C_j$,y,$\Sigma_{j \in \mathcal{K}} \rho_j$) outputs TRUE.

Process 2: LiSA secure aggregation protocol with integrity. Parties: Server and users $\mathcal{U} = [n]$. Public parameters: input domain $\mathbb{X}$, fraction of drop-outs $\delta$, fraction of corruptions y, security parameter for cryptographic primitives $\lambda$, committee size k, backup-set size $\ell$, secret sharing reconstruction threshold t, minimum fraction of aggregated inputs $\alpha$, maximum number of corrupt super-clients $\tilde{c}$. Prerequisites: Each user $i \in \mathcal{U}$ has key-pairs computed as $(sk_i, pk_i) \leftarrow KA.Gen(1^\lambda)$, $(SK_i, PK_i) \leftarrow KA.Gen(1^\lambda)$ and $$(sk_i^s, pk_i^s) \leftarrow DS.Gen(1^\lambda);\ \text{public keys } (pk_i, PK_i, pk_i^s)$$

are registered with the PKI.

For $\mathcal{U}$ and $r \in [6]$ and, we denote by $\mathcal{U}_r$ the set of users that complete the execution of round r without dropping out, and we denote by $$\mathcal{U}_r'$$

the set of users the server knows have completed round r. It holds $$\mathcal{U}_r' \subseteq \mathcal{U}_r \subseteq \mathcal{U}_{r-1}$$

for all $r \in [6]$.

Round 1: each party (1) receives random seed Q; and (2) selects committee of super-clients $\mathcal{K} \leftarrow Select(Q, \mathcal{U}, k)$.

Round 2: a super-client $j \in \mathcal{K}$ (1) selects backup sets $\mathcal{L}_j \leftarrow Select(Q \| j, \mathcal{U} \setminus \{j\}, \ell)$; (2) fetches public keys of backup clients $\{pk_i\}_{i \in \mathcal{L}_j}$ from the PKI; (3) derives symmetric keys:

$$\left\{k_{j,i}^e \leftarrow KA(\text{``ENC''}; sk_j, pk_i)\right\}_{i \in \mathcal{L}_j};$$

(4) secret shares key $SK_j$:$\{S_{i,j}\}_{i \in \mathcal{L}_j} \leftarrow SS.Share(\ell; t; SK_j)$; (5) encrypts shares of $$SK_j: \left\{E_{j,i} \leftarrow AE.Enc\left(k_{j,i}^e, S_{j,i}\right)\right\}_{i \in \mathcal{L}_j};$$

and (6) sends $\{j; i; E_{j,i}\}_{i \in \mathcal{L}_i}$ to the server. A user $i \in \mathcal{U}$ (1) fetches public keys $\{PK_j\}_{j \in \mathcal{K}}$ from the PKI; (2) derives symmetric keys:

$$\{k_{i,j}^* \leftarrow KA(\text{``PRG''}; sk_i, PK_j)\}_{j \in \mathcal{K}};$$

(3) computes blinded input:

$$c_i \leftarrow x_i + \sum_{j \in k} F(k_{i,j}^*); \tag{4}$$

sends $c_i$ to the server; (5) computes commitment to $x_i$: $\text{comm}_i \leftarrow \text{COMM.Gen}(x_i, r_i)$ where $r_i$ is a random value; (6) computes signature on $\text{comm}_i$:

$$\sigma_i \leftarrow DS.Sign(sk_i^s; comm_i);$$

(7) computes k-out-of-k shares of $r_i$: $\{r_{i,j}\}_{j \in \mathcal{K}} \leftarrow \text{SS.Share}$ (k,k;$r_i$); (8) derives symmetric keys:

$$\{k_{i,j}^s \leftarrow KA(\text{``ENC''}; sk_i, PK_j)\}_{j \in \mathcal{K}};$$

(9) encrypts the random shares of $$r_i: \{E_{i,j}^s \leftarrow AE.Enc(k_{i,j}^s, r_{i,j})\}_{j \in \mathcal{K}};$$

and (10) sends $$\{(i; j; E_{i,j}^s)\}_{j \in \mathcal{K}},$$

$(\text{comm}_i, \sigma_i)$ to the server.

Round 3: a server (1) receives encrypted key shares $\{(j;i;E_{j,i})\}_{i \in \mathcal{L}_j}$ from $j \in \mathcal{K} \cap \mathcal{U}'_2$ and sends each of them to corresponding backup client; (2) receives blinded inputs $c_i$ from users $i \in \mathcal{U}'_2$; (3) aggregates input $c_{agg} \leftarrow \Sigma_{i \in \mathcal{U}'_2} c_i$; (4) sends $$\mathcal{U}'_2$$

to super-clients in $$j \in \mathcal{K} \cap \mathcal{U}'_2;$$

(5) receives encrypted random shares $$\{(i; j; E_{i,j}^s)\}_{j \in \mathcal{K}}$$

from $$i \in \mathcal{U}'_2$$

and sends each of them to the corresponding super-client; and (6) receives commitments and signatures $\{(\text{comm}_i, \sigma_i)\}_{i \in \mathcal{U}'_2}$ and sends all of them to all super-clients. A super-client $$j \in \mathcal{K} \cap \mathcal{U}'_2 \tag{1}$$

receives $$\mathcal{U}'_2$$

from the server; (2) if $$|\mathcal{U}'_2| < \alpha n,$$

aborts; (3) receives commitments and signatures $\{(\text{comm}_i, \sigma_i)\}_{i \in \mathcal{U}'_2}$; (4) asserts that signatures are valid: if $$\left|\{i \in \mathcal{U}'_2: DS.Verif(pk_i^s; \sigma_i; comm_i) == TRUE\}\right| < |\mathcal{U}'_2|,$$

then aborts; (5) aggregates the commitments: $C_j = \bigodot_{i \in \mathcal{U}'_2} \text{comm}_i$; (6) signs the aggregate commitment and set $$\mathcal{U}'_2:$$

$$\sigma_j^C \leftarrow DS.Sign(sk_j^s; C_j || \mathcal{U}'_2);$$

(7) receives encrypted random shares:

$$\{(i; j; E_{i,j}^s)\}_{i \in \mathcal{U}'_2}; \tag{8}$$

derives symmetric keys $$\{k_{j,i}^s \leftarrow KA(\text{``ENC''}; SK_j, pk_i)\}_{i \in \mathcal{U}'_2};$$

(9) decrypts random shares $$\{r_{i,j}, \leftarrow AE.Dec(k_{j,i}^s; E_{ij})\}_{i \in \mathcal{U}'_2};$$

(10) computes the sum or random shares $\rho_j = \Sigma_{i \in \mathcal{U}'_2} r_{i,j}$; (11) signs the sum or random shares $$\sigma_j^\rho \leftarrow DS.Sign(sk_j^s; \rho_j);$$

(12) sends $$\rho_j, \sigma_j^\rho, C_j, \sigma_j^C$$

to the server; (13) fetches public keys $\{pk_i\}_{i \in \mathcal{U}_2'}$ from the PKI; (14) derives symmetric keys $$\{k_{j,i}^* \leftarrow KA(\text{``PRG''}; SK_j, pk_i)\}_{i \in \mathcal{U}_2'};$$

(15) computes partial blinding $$\partial j \leftarrow \Sigma_{i \in \mathcal{U}_2'} F(k_{j,i}^*);$$

and (16) sends $\partial_j$ to the server.

Round 4: a server, when $$// \mathcal{K}_{alive} := \mathcal{K} \cap \mathcal{U}_3' \text{ and } \mathcal{K}_{drop} := \mathcal{K} \backslash \mathcal{K}_{alive}$$

and $\mathcal{L} = \cup_{j \in \mathcal{K}} \mathcal{L}_j$ (1) receives $$\{(\rho_j, \sigma_j^\rho, C_j, \sigma_j^C)\}_{j \in \mathcal{K}_{alive}}$$

from super-clients in $\mathcal{K}_{alive}$; (2) receives $\{\partial_j\}_{j \in \mathcal{K}_{alive}}$ from super-clients in $\mathcal{K}_{alive}$; (3) if $|\mathcal{K}_{alive}| = k$ jumps to step (2) of Round 6; (4) sends $\mathcal{K}_{drop}$ to all users in $\mathcal{L}$. A backup client $i \in \mathcal{L}$ (1) receives $\mathcal{K}_{drop}$ from the server; (2) if $|\mathcal{K}_{drop}| \geq k-\tilde{c}$, then aborts; (3) computes signature $$\sigma_i \leftarrow DS.Sign(sk_i^s; \mathcal{K}_{drop});$$

and (4) sends $\sigma_i$ to the server.

Round 5: a server (1) receives $\{\sigma_i\}_{i \in \mathcal{L} \cap \mathcal{U}_3'}$ from users $$\mathcal{L} \cap \mathcal{U}_3'$$

and forwards them to all users in $$\mathcal{L} \cap \mathcal{U}_3'.$$

A backup client $$i \in \mathcal{L} \cap \mathcal{U}_3' \tag{1}$$

receives $\{\sigma_i\}_{i \in \mathcal{L} \cap \mathcal{U}_3'}$; (2) fetches $$\{pk_i^s\}_{i \in \mathcal{L} \cap \mathcal{U}_3'}$$

from the PKI; (3) computes $$\mathcal{L}_{ack} = \{l \in (\mathcal{L} \cap \mathcal{U}_4') : DS. \; Verif(pk_l^s, \sigma_l, \mathcal{K}_{drop}) = TRUE\};$$

(4) if $|\mathcal{L}_j \cap \mathcal{L}_{ack}| < t$ for any $j \in \mathcal{K}$, then aborts; and (5) for any $j \in \mathcal{K}_{drop}$ such that $i \in \mathcal{L}_j$: (a) fetches $pk_j$ from the PKI; (b) derives symmetric key $$(k_{i,j}^e) \leftarrow KA(\text{``ENC''}; sk_i, pk_j);$$

(c) decrypts $$S_{j,i} \leftarrow AE.Dec(k_{i,j}^e; E_{j,i});$$

and (d) sends $S_{j,i}$ to the server.

Round 6: a server (1) for each $j \in \mathcal{K}_{drop}$: (a) collects shares $\{S_{j,i}\}_{i \in \mathcal{L}_j \cap \mathcal{U}_5'}$ and aborts if receives less than t shares; (b) reconstructs secret key $SK_j \leftarrow SS.Rec(\{S_{j,i}\}_{i \in \mathcal{L}_j \cap \mathcal{U}_5'})$; (c) derives symmetric keys $$\{k_{j,i}^* \leftarrow KA(\text{``PRG''}; SK_j; pk_i)\}_{i \in \mathcal{U}_2'};$$

(d) computes missing partial blinding $$\partial_j' \leftarrow \sum_{i \in \mathcal{U}_2'} F(k_{i,j}^*);$$

(e) derives symmetric keys $$\{k_{j,i}^s \leftarrow KA(\text{``ENC''}; SK_j; pk_i)\}_{i \in \mathcal{U}_2'};$$

(f) decrypt random shares $$\{r_{i,j} \leftarrow AE. \; Dec(k_{j,i}^s; E_{i,j})\}_{i \in \mathcal{U}_2'};$$

(g) computes the sum or random shares $\rho_j = \Sigma_{i \in \mathcal{U}_2'} r_{i,j}$; (2) given $\{\partial_j\}_{j \in \mathcal{K}} = \{\partial_j\}_{j \in \mathcal{K}_{alive}} \cup \{\partial_j\}_{j \in \mathcal{K}_{drop}}$, computes the output: $y \leftarrow c\_agg - \Sigma_{j \in \mathcal{K}} \partial_j$; and (3) publishes y and $$\mathcal{U}_2'$$

and $$\{(\rho_j, \sigma_j^\rho, C_j, \sigma_j^C)\}_{j \in \mathcal{K}_{alive}}$$

and $\{\rho_j\}_{j \in \mathcal{K}_{drop}}$. A user i (1) fetches

29

$$\{pk_j^s\}_{j \in \mathcal{K}_{alive}}$$

from the PKI; and (2) asserts the following: (a) $|\mathcal{K}_{alive}| \geq k - \tilde{c}$; (b) for all pair of indices $$j_1, j_2 \in K_{alive}: C_{j_1} == C_{j_2}; (c) \; DS. \; Verif\left(pk_j^s; \sigma_j^\rho; \rho_j\right) == j \in \mathcal{K} \text{ alive;}$$

$$(d) \; DS. \; Verif\left(pk_j^s; \sigma_j^C; C_j \parallel \mathcal{U}_2'\right) == \text{TRUE for } j \in \mathcal{K} \text{ alive;}$$

and (e) COMM.Vfy($C_j$,y,$\Sigma_{j \in \mathcal{K}} \; \rho_j$)==TRUE.

While subject matter of the present disclosure has been illustrated and described in detail in the drawings and foregoing description, such illustration and description are to be considered illustrative or exemplary and not restrictive. Any statement made herein characterizing the invention is also to be considered illustrative or exemplary and not restrictive as the invention is defined by the claims. It will be understood that changes and modifications may be made, by those of ordinary skill in the art, within the scope of the following claims, which may include any combination of features from different embodiments described above.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

What is claimed is:

1. A computer-implemented method for secure aggregation, by a server of a distributed client-server application, of client-provided inputs in a manner allowing for integrity verification, the method comprising:

receiving, from each of a plurality of clients, a respective client input, for which a commitment to the respective client input is published, the commitments having been computed using randomness, and the commitments being aggregated by at least two super-clients and a sum of the aggregated commitments being published by each of the at least two super-clients;

obtaining a sum of the received client inputs; and publishing the sum of the received client inputs such that validity of the sum of the received client inputs is checkable, by one or more of the clients, by comparing the sum of the received client inputs to a result of a verification algorithm that uses a sum of additive shares that were computed by the clients using the randomness, and by verifying that the published sum of the aggregated commitments is the same for each of the at least two super-clients,

wherein the randomness is different for different clients, and wherein the randomness can only be reconstructed if all of the additive shares for a respective one of the clients are available.

2. The method of claim 1, wherein the at least two super-clients, and/or at least two other super-clients, receive and publish different additive shares of a same client along with additional additive shares from other clients such that no super-client obtains all additive shares of a same client, and such that the sum of all additive shares is obtainable by summing the additive shares published by the at least two super-clients and/or the at least two other super-clients.

3. The method of claim 1, wherein a number of the super-clients to be used for the secure aggregation is determined from a random beacon, and wherein a number of the additive shares computed per client corresponds to the number of the super-clients such that each of the super-clients receives one additive share per client.

4. The method of claim 3, wherein the number of the super-clients to be used for the secure aggregation is determined using a pseudo-random function which takes as input a random seed generated by the random beacon and public keys of the clients.

5. The method of claim 1, wherein at least one backup client is selected for each of the at least two super-clients, the backup client in each case having a secret key of a corresponding one of the super-clients.

6. The method of claim 5, wherein the server receives the secret key from the corresponding one of the super-clients and sends the secret key to a corresponding one of the backup clients.

7. The method of claim 5, wherein a set of backup clients are selected for each of the at least two super-clients, and wherein a secret sharing reconstruction threshold is less than a number of backup clients in the set so as to allow for a dropout of at least one of the at least two super-clients.

8. The method of claim 1, wherein the client inputs are blinded using a mask using a key shared with one of the at least two super-clients.

9. The method of claim 8, further comprising receiving, from each of the at least two super-clients, a partial blinding that was computed by a respective one of the super-clients by summing the masks received by the respective super-client from different ones of the clients, wherein obtaining the sum of the received client inputs includes aggregating the blinded client inputs and subtracting a sum of the partial blindings.

10. The method of claim 1, wherein the commitments are determined using a linearly-homomorphic commitment scheme.

11. The method of claim 1, wherein the client inputs are from medical records and/or independent healthcare facilities, and wherein the sum of the received client inputs is used for training a model for medical diagnostics or for monitoring health status of patients.

12. The method of claim 1, wherein the client inputs are from sensors of a smartcity application, and wherein the sum of the client inputs are used to determine a condition in the smartcity application.

13. A computer system for secure aggregation, by a server of a distributed client-server application, of client-provided inputs in a manner allowing for integrity verification, the system comprising one or more hardware processors which, alone or in combination, are configured to provide for execution of the method according to claim 1.

14. A tangible, non-transitory computer-readable medium having instructions thereon for secure aggregation, by a server of a distributed client-server application, of client-provided inputs in a manner allowing for integrity verification, the instructions, upon being executed by one or more hardware processors, alone or in combination, providing for execution of the method according to claim 1.

15. The method of claim 1, wherein the commitments have each been computed using a commitment scheme run by a sender that receives as input a message of the sender and a random value chosen by the sender to output the respective commitment, such that validity of the respective commitment is checkable by a verification scheme that takes as input the message, the random value and the respective commitment to verify that the respective commitment was correctly computed using the message and the random value.

16. The method of claim 1, wherein a number of the additive shares computed per client corresponds to a number of the super-clients such that each of the super-clients receives one additive share per client.

17. The method of claim 1, wherein the commitment is published by providing the commitment to each of the plurality of clients.

18. A computer-implemented method for secure aggregation, by a server of a distributed client-server application, of client-provided inputs in a manner allowing for integrity verification, the method comprising:

receiving, from each of a plurality of clients, a respective client input, for which a commitment to the respective client input is published, the commitments having been computed using randomness, and the commitments being aggregated by at least two super-clients and a sum of the aggregated commitments being published by each of the at least two super-clients;

obtaining a sum of the received client inputs; and publishing the sum of the received client inputs such that validity of the sum of the received client inputs is checkable, by one or more of the clients, by comparing the sum of the received client inputs to a result of a verification algorithm that uses a sum of additive shares that were computed by the clients using the randomness, and by verifying that the published sum of the aggregated commitments is the same for each of the at least two super-clients, wherein a number of the super-clients to be used for the secure aggregation is determined from a random beacon, and wherein a number of the additive shares computed per client corresponds to the number of the super-clients such that each of the super-clients receives one additive share per client.

19. The method of claim 18, wherein the number of the super-clients to be used for the secure aggregation is determined using a pseudo-random function which takes as input a random seed generated by the random beacon and public keys of the clients.

20. A computer-implemented method for secure aggregation, by a server of a distributed client-server application, of client-provided inputs in a manner allowing for integrity verification, the method comprising:

receiving, from each of a plurality of clients, a respective client input, for which a commitment to the respective client input is published, wherein the commitments have been computed using randomness, wherein the commitments are aggregated by at least two super-clients and a sum of the aggregated commitments is published by each of the at least two super-clients, and wherein the client inputs are blinded using a mask using a key shared with one of the at least two super-clients;

receiving, from each of the at least two super-clients, a partial blinding that was computed by a respective one of the super-clients by summing the masks received by the respective super-client from different ones of the clients;

obtaining a sum of the received client inputs including aggregating the blinded client inputs and subtracting a sum of the partial blindings; and publishing the sum of the received client inputs such that validity of the sum of the received client inputs is checkable, by one or more of the clients, by comparing the sum of the received client inputs to a result of a verification algorithm that uses a sum of additive shares that were computed by the clients using the randomness, and by verifying that the published sum of the aggregated commitments is the same for each of the at least two super-clients.

* * * * *